United States Patent
Chen et al.

(10) Patent No.: US 10,501,452 B2
(45) Date of Patent: Dec. 10, 2019

(54) LACTAM COMPOUND DERIVATIVE AND APPLICATION THEREOF

(71) Applicant: NHWA PHARMA. CORPORATION, Xuzhou, Jiangsu (CN)

(72) Inventors: Yin Chen, Xuzhou (CN); Fei Dou, Xuzhou (CN); Yinli Qiu, Xuzhou (CN); Minquan Yu, Xuzhou (CN); Guisen Zhang, Xuzhou (CN)

(73) Assignee: NHWA PHARMA. CORPORATION, Xuzhou (CN)

( * ) Notice: Subject to any disclaimer, the term of this patent is extended or adjusted under 35 U.S.C. 154(b) by 0 days.

(21) Appl. No.: 15/776,645

(22) PCT Filed: Nov. 21, 2016

(86) PCT No.: PCT/CN2016/106591
§ 371 (c)(1),
(2) Date: May 16, 2018

(87) PCT Pub. No.: WO2017/084627
PCT Pub. Date: May 26, 2017

(65) Prior Publication Data
US 2018/0327397 A1    Nov. 15, 2018

(30) Foreign Application Priority Data
Nov. 20, 2015    (CN) .......................... 2015 1 0811995

(51) Int. Cl.
| | | |
|---|---|---|
| *C07D 413/14* | (2006.01) | |
| *C07D 221/04* | (2006.01) | |
| *A61K 31/4725* | (2006.01) | |
| *A61K 31/496* | (2006.01) | |
| *A61K 31/506* | (2006.01) | |
| *A61K 31/517* | (2006.01) | |
| *C07D 217/24* | (2006.01) | |
| *C07D 401/12* | (2006.01) | |
| *C07D 405/12* | (2006.01) | |
| *C07D 239/88* | (2006.01) | |
| *C07D 239/90* | (2006.01) | |
| *C07D 417/12* | (2006.01) | |
| *C07D 409/12* | (2006.01) | |

(52) U.S. Cl.
CPC ........ *C07D 413/14* (2013.01); *A61K 31/4725* (2013.01); *A61K 31/496* (2013.01); *A61K 31/506* (2013.01); *A61K 31/517* (2013.01); *C07D 217/24* (2013.01); *C07D 221/04* (2013.01); *C07D 239/88* (2013.01); *C07D 239/90* (2013.01); *C07D 401/12* (2013.01); *C07D 405/12* (2013.01); *C07D 409/12* (2013.01); *C07D 417/12* (2013.01)

(58) Field of Classification Search
CPC . C07D 221/04; C07D 413/14; A61K 31/4725
See application file for complete search history.

(56) References Cited

U.S. PATENT DOCUMENTS

2011/0160199 A1    6/2011    Li et al.

FOREIGN PATENT DOCUMENTS

| CN | 104059046 A | 9/2014 |
|---|---|---|
| JP | 02191256 | 7/1990 |
| JP | 2006503106 | 1/2006 |
| JP | 2006316052 A | 11/2006 |
| JP | 2010521528 A | 6/2010 |
| JP | 2011529090 A | 12/2011 |
| WO | WO-2004026864 A1 | 4/2004 |
| WO | WO-2006112464 A1 | 10/2006 |
| WO | WO-2007026959 A2 | 3/2007 |
| WO | WO-2008020306 A2 | 2/2008 |
| WO | WO-2008113559 A2 | 9/2008 |
| WO | WO-2012003418 A2 | 1/2012 |
| WO | WO-2014146553 A1 | 9/2014 |

OTHER PUBLICATIONS

Hecker, Scott J., et al., "Prodrugs of phosphates and phosphonates", Journal of medicinal chemistry 51.8, (2008), 2328-2345.
Higuchi, Takeru, et al., "Pro-drugs as novel drug delivery systems", American Chemical Society, (1975), 249 pgs.
Rautio, Jarkko, et al., "Prodrugs: design and clinical applications", Nature Reviews Drug Discovery 7.3, (2008), 255-270.
Roche, Edward B., "Bioreversible Carriers in Drug Design, American Pharmaceutical Association and Pergamon Press, 1987", (1987), 3 pgs.
"International Application No. PCT/CN2016/106591, International Search Report dated Mar. 1, 2017", w/ English Translation, (Mar. 1, 2017), 3 pgs.

(Continued)

*Primary Examiner* — Karen Cheng
(74) *Attorney, Agent, or Firm* — Schwegman Lundberg & Woessner, P.A.

(57) ABSTRACT

The present invention relates to a lactam compound derivative, a medicine composition comprising the lactam compound derivative, and uses of the composition and the lactam compound derivative in preparation of a medicine for preventing or treating schizophrenia, the lactam compound derivative having a structure as shown in Formula I.

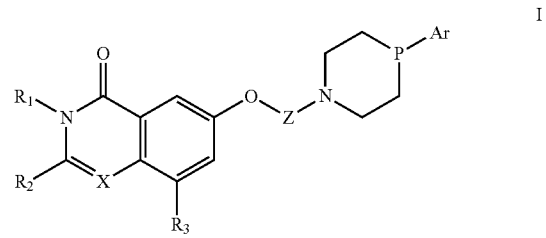

14 Claims, No Drawings

(56) References Cited

OTHER PUBLICATIONS

"International Application No. PCT/CN2016/106591, Written Opinion dated Mar. 1, 2017", (Mar. 1, 2017), 3 pgs.
"European Application U.S. Appl. No. 16865804.5, Extended European Search Report dated Jun. 19, 2019", (Jun. 19, 2019), 10 pgs.
"Japanese Appliccation U.S. Appl. No. 2018-526201, Notification of Refusal dated (May 30, 2019", w/ English Translation, (May 30, 2019), 8 pgs.
Caldas, Giovana Baptista, et al., "Application of 4D-QSAR studies to a series of benzothiophene analogs", Journal of molecular modeling 20.10, (Sep. 16, 2014), 2420.

LACTAM COMPOUND DERIVATIVE AND APPLICATION THEREOF

PRIORITY APPLICATIONS

This application is a U.S. National Stage Filing under 35 U.S.C. 371 from International Application No. PCT/CN2016/106591, filed on Nov. 21, 2016, and published as WO2017/084627 on May 26, 2017, which claims the benefit of priority to Chinese Application No. 201510811995.4, filed on Nov. 20, 2015; the benefit of priority of each of which is hereby claimed herein, and which applications and publication are hereby incorporated herein by reference in their entirety.

TECHNICAL FIELD

The invention relates to the field of medicine and particularly relates to a lactam compound derivative, a pharmaceutical composition comprising the same, and use of the pharmaceutical composition and the lactam compound derivative in the manufacture of a medicament for the prevention or treatment of schizophrenia.

BACKGROUND

Schizophrenia is the most serious and most harmful disease among all mental illnesses. The global morbidity is about 1-2%. The lifetime prevalence of schizophrenia patients is 0.7-0.8%, which is not significantly relevant to gender, race, or social boundaries. Meanwhile, the mortality of schizophrenia patients is 2-3 times higher than that of the general population. Recent studies have shown that the social burden of mental illness ranks first among diseases in China, exceeding diseases such as cardiovascular, respiratory diseases and malignant tumors.

There are two major types of drug for schizophrenia, i.e. "typical" anti-schizophrenia drug and "non-typical" anti-schizophrenia drug. Typical anti-schizophrenia drug (e.g. chloropromazine and haloperidol) which blocks dopamine $D_2$ receptor has good therapeutic effect on positive symptoms of schizophrenia. But due to the strong blocking on dopamine $D_2$ receptor, it will lead to side effects like extrapyramidal system (EPS) reaction, tardive dyskinesia and increase of prolactin. Furthermore, it is not effective for negative symptoms of schizophrenia.

Non-typical anti-schizophrenia drug represented by clozapine and risperidone has strong effect on not only dopamine ($D_2$) receptor, but also 5-hydroxytryptamine ($5-HT_{2A}$) receptor. These drugs provide significant advantages over typical anti-schizophrenia drug: good therapeutic effect against schizophrenia positive symptoms, significantly reduced side effects of extrapyramidal system reaction and tardive dyskinesia or the like, and some non-typical anti-schizophrenia drugs can improve the negative symptoms and cognitive disorders in some degree. However, all the non-typical anti-schizophrenia drugs in current clinical application have side effects of extended QT interval, hyperprolactine or the like in varying degrees. Therefore, it is important to find a new drug which can effectively cure schizophrenia, and has less side effects.

Studies have shown that receptors like $D_2$, $5-HT_{1A}$, $5-HT_{2A}$ and $H_1$ play a very important role in schizophrenia. Action with $D_2$ receptor may be effective for the treatment of schizophrenia positive symptoms. The pyramidal neurons and GABA interneurons of prefrontal cortex comprise 5-hydroxytryptamine receptor $5-HT_{1A}$ and $5-HT_{2A}$. 5-hydroxytryptamine system plays an important role in modulating the function of prefrontal cortex, including emotion control, cognitive behavior and working memory. $5-HT_{1A}$ is associated with the effect of non-typical anti-psychosis drug therapy, which can improve negative symptoms and cognitive disorders. $5-HT_{2A}$ receptor relates to various aspects, including cognition, emotion regulation and motion control. The blocking of $5-HT_{2A}$ receptor can normalize the release of dopamine, exerting the effect of anti-psychosis. mRNA of $5-HT_7$ receptor is expressed in peripheral tissue as well as the central nervous system, wherein it is mainly located in thalamus, hypothalamus, cerebral cortex, hippocampus and amygdala. This receptor can modulate body temperature, biological rhythm, sleeping, emotion, learning and memory. $5-HT_7$ receptor is important for the modulation of central nervous system activities in normal and pathologic conditions, and can be utilized as an important target for mental disease treatment. Meanwhile, during long-term medication for schizophrenia treatment, some drugs are liable to bring about the side effect of bodyweight gain. Studies have shown that these side effects are closely related with histamine $H_1$ receptor.

Therefore, it is desirable for novel anti-schizophrenia drug to have multiple receptors binding, broad range of activity, and reduced side effects of EPS and bodyweight gain or the like.

SUMMARY

In an aspect, provided is a compound of Formula I or a pharmaceutically acceptable salt or prodrug thereof,

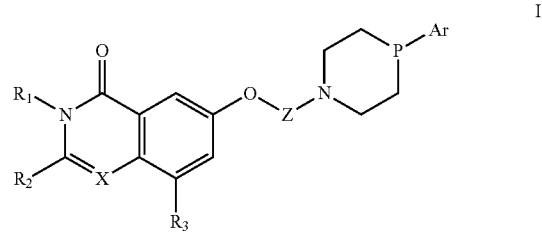

wherein,

X is C, O, N or NH;

Z is $-(CH_2)_n-$, which is unsubstituted or substituted by one or more substituents selected from the group consisting of alkyl, cyano, hydroxy and halogen, n is an integer of 2~7;

$R_1$ and $R_2$ are each independently hydrogen, or linear or branched alkyl containing 1~5 carbon atoms, wherein the alkyl is optionally substituted by one or more substituents selected from the group consisting of alkyl, cyano, hydroxy and halogen;

$R_3$ is hydrogen, halogen or linear or branched alkyl containing 1~5 carbon atoms, wherein the alkyl is optionally substituted by one or more substituents selected from the group consisting of alkyl, cyano, hydroxy and halogen;

P is CH or N;

Ar is a group selected from the group consisting of formula II-VII:

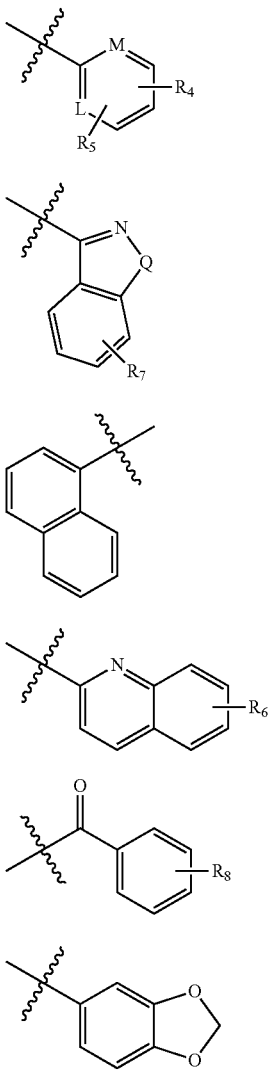

L and M are independently CH or N;
Q is O or S;
$R_4$, $R_5$, $R_6$, $R_7$ and $R_8$ are each independently hydrogen, halogen, linear or branched alkyl containing 1~5 carbon atoms, or alkoxyl containing 1~5 carbon atoms, wherein the alkyl and alkoxyl are optionally substituted by one or more substituents selected from the group consisting of alkyl, cyano, hydroxy and halogen.

In another aspect, provided is further a pharmaceutical composition, which comprises a compound or a pharmaceutically acceptable salt or prodrug thereof according to the invention, and pharmaceutically acceptable excipient, carrier, adjuvant, solvent or the combination thereof.

In another aspect, provided is a compound or a pharmaceutically acceptable salt or a prodrug thereof according to the invention or a pharmaceutical composition according to the invention for use in the prevention or treatment of neuropsychiatric disease, in particular schizophrenia.

Provided is also a method for the prevention or treatment of neuropsychiatric disease, in particular schizophrenia, comprising administrating a subject in need thereof a compound or a pharmaceutically acceptable salt or a prodrug thereof according to the invention or a pharmaceutical composition according to the invention in an effective amount.

Provided is also use of a compound according to the invention, or a pharmaceutically acceptable salt or a prodrug thereof, or a pharmaceutical composition according to the invention, in the manufacture of a medicament for the treatment or prevention of neuropsychiatric disease, in particular schizophrenia.

DETAILED DESCRIPTION OF THE INVENTION

Definitions and General Terms

Unless indicated otherwise, definitions used herein should be adopted as follows. For the purpose of the invention, chemical elements should be consistent with the CAS version of Periodic Table of Elements and *Handbook of Chemistry and Physics* (the 75$^{th}$ edition, 1994). In addition, general principles of organic chemistry may refer to "*Organic Chemistry*", Thomas Sorrell, University Science Books, Sausalito: 1999 and "*March's Advanced Organic Chemistry*", Michael B. Smith and Jerry March, John Wiley & Sons, New York: 2007, which are incorporated herein by reference in their entirety.

The term "patient" or "subject" used in the invention refers to human (including adult and child) or other animal (including mammal). According to some examples of the invention, "patient" or "subject" refers to human.

The term "optional" or "optionally" or "optionally exist" means the event described subsequent thereto may, but not necessarily happen, and the description includes the cases wherein the said event or circumstance happens or does not happen. For example, "a bond optionally exists" refers to a bond which may exist or not exist, and the description includes single bond, double bond or triple bond.

The term "optionally substituted" can be exchangeablly used with the term "substituted or unsubstituted" in the invention. Generally, the term "substituted" means that one or more hydrogen atoms in the given structure are substituted by a specific substituent. Unless stated in other aspects, an optionally substituted group can be substituted at each substitutable site on it. When more than one site in the given structure can be substituted by one or more substituents selected from the group consisting of specific groups, each site can be substituted by the same or different substituents.

Unless otherwise indicated clearly, the description "(each) independently" used herein should be understood in a broad sense. It may mean that the specific options denoted by the same symbol in different groups have no influence upon each other, or may also mean that the specific options denoted by the same symbol in the same group have no influence upon each other.

In the sections of the description, substituents of the compound of the invention are disclosed according to the types and scopes of the groups. It should be particularly indicated that, every independent subordinated combination of the types and scopes of these groups are encompassed by invention. For example, the term "$C_{1-5}$ alkyl" particularly means independently disclosed methyl, ethyl, $C_3$ alkyl, $C_4$ alkyl and $C_5$ alkyl.

The ranges described herein (like numerical ranges) may include every value within the range, and every subrange constituted by each value. For example, "n is an integer of "2~7" includes 2, 3, 4, 5, 6 or 7, and every subrange constituted by these value, including but not limited to 2~6, 2~5, 2~4, 3~6, 3~5, 4~6, etc.

The description "one or more" used herein can mean 1, 2, 3, 4, 5, 6, 7 or more.

In Formula I, the dashed line-containing portion may represent a single bond or a double bond. A person of skill in the art should readily understand that for consideration of rational selection of chemical bonds and obtaining stable compounds, in the cases of a single bond or a double bond, the atom or radical denoted by X may be correspondingly and optionally attached with one or more hydrogen atoms. For example, if the dashed line-containing portion represents a single bond, when X is selected as C, it should be understood that it may correspondingly represent $CH_2$. If the dashed line-containing portion represents a double bond, when X is selected as C, it should be understood that it may correspondingly represent CH. Likewise, if the dashed line-containing portion represents a double bond, a person of skill in the art would understand that for the purposes of reasonable selection of chemical bonds and obtaining stable compounds, the choice of X as NH may correspondingly represent N. In one embodiment, the aforementioned atomic group (eg. CH, $CH_2$, NH) may be optionally substituted, for example by one or more substituents selected from alkyl, cyano, hydroxyl and halogen.

Unless specifically indicated, the term "alkyl" or "alkyl group", represent saturated linear or branched monovalent hydrocarbyl group containing 1 to 20 carbon atoms, wherein the alkyl group may be optionally substituted by one or more the substituents according to the invention. Unless specifically indicated otherwise, alkyl group contains 1 to 20 carbon atoms. According to an embodiment of the invention, the alkyl group contains 1 to 12 carbon atoms. According to another embodiment of the invention, the alkyl group contains 1 to 6 carbon atoms. According to an embodiment of the invention, the alkyl group contains 1 to 5 or 1 to 4 carbon atoms. According to another embodiment of the invention, the alkyl group contains 1 to 3 carbon atoms. Examples of the alkyl groups include but are not limited to methyl (Me, —$CH_3$), ethyl (Et, —$CH_2CH_3$), n-propyl (n-Pr, —$CH_2CH_2CH_3$), iso-propyl (i-Pr, —$CH(CH_3)_2$), n-butyl (n-Bu, —$CH_2CH_2CH_2CH_3$), iso-butyl (i-Bu, —$CH_2CH(CH_3)_2$), secondary butyl (s-Bu, —$CH(CH_3)CH_2CH_3$), tertiary butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), n-heptyl, n-octyl, etc.

The term "halogen" refers to fluorine (F), chlorine (Cl), bromine (Br) or iodine (I).

The term "alkoxyl containing 1~5 carbon atoms" refers to an alkyl group attached to the rest of the molecule through oxygen atom, wherein the alkyl group has the meaning defined hereinabove. Unless specifically indicated otherwise, the alkoxyl group may contain 1 to 5 carbon atoms. Examples of alkoxyl group include, but are not limited to, methoxyl (MeO, —$OCH_3$), ethoxyl (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentyloxy (n-pentyloxy, —$OCH_2CH_2CH_2CH_2CH_3$), 2-pentyloxy (—$OCH(CH_3)CH_2CH_2CH_3$), 3-pentyloxy (—$OCH(CH_2CH_3)_2$), etc.

The term "pharmaceutically acceptable salt" refers to an organic salt and an inorganic salt of the compound according to the invention. The pharmaceutically acceptable salt is known to us, like those recited in the literature: S. M. Berge et al., J. Pharmaceutical Sciences, 66: 1-19, 1977. Pharmaceutically acceptable salts formed by non-toxic acids include, but are not limited to, a salt formed by reaction with an inorganic acid, e.g. hydrochloride, hydrobromate, phosphate, sulfate, perchlorate; and a salt formed by reaction with an organic acid, e.g. acetate, oxalate, maleate, tartrate, citrate, succinate, malonate; or these salts can be obtained through other methods recited in the literatures, like ion exchange. Other pharmaceutically acceptable salts include but are not limited to adipate, alginate, ascorbate, aspartate, benzenesulphonate, benzoate, bisulphate, borate, butyrate, camphorate, camphorsulfonate, cyclic pentyl propionate, digluconate, dodecyl sulfates, ethanesulfonate, formate, fumarate, glucoheptonate, glycerin phosphate, glyconate, hemisulphate, heptylate, hexanoate, hydriodate, 2-hydroxyethanesulfonate, lactobionate, lactate, laurate, lauryl sulfate, malate, malonate, methanesulfonate, 2-naphthalenesulfonate, nicotinate, nitrate, oleate, palmitate, pamoate, pectate, persulphate, 3-phenylpropionate, picrate, pivalate, propionate, stearate, thiocyanate, p-methylbenzenesulphonate, undecylate, valerate, etc. Salts obtained from suitable bases include but are not limited to salts of alkali metal, alkali-earth metal, ammonium and $N^+(C_{1-4} alkyl)_4$.

The term "treatment" can refer to ameliorating a disease or disorder (ie, slowing or preventing or reducing the disease or the development of at least one clinical symptom thereof). In other embodiments, "treatment" refers to alleviating or ameliorating at least one physical parameter, including physical parameters that may not be perceived by the patient. In other embodiments, "treatment" refers to modulating a disease or disorder physically (eg, stabilizing a visible symptom) or physiologically (eg., stabilizing a parameter of the body), or both. In other embodiments, "treatment" refers to preventing or delaying the onset, occurrence or exacerbation of a disease or disorder.

The term "prevention" refers to a decrease in the risk of developing a disease or disorder (ie, ceases the development of at least one clinical symptom of a disease in a subject that may face or tend to face this disease, but has not yet experienced or manifested the symptoms of the disease).

The pharmaceutically acceptable salts of the invention may be prepared from the parent compound, basic or acidic moiety through conventional chemical procedures. Generally, such salts may be prepared through the reaction of the compounds in the form of free acid with stoichiometric appropriate base (e.g. carbonate, bicarbonate, hydroxide of Na, Ca, Mg or K, etc.) or through the reaction of the compounds in the form of free base with stoichiometric appropriate acid. Such reactions are often performed in water, organic solvent or the mixture thereof. Typically, in suitable cases, nonaqueous medium like ether, ethyl acetate, ethanol, isopropanol and/or acetonitrile are required. A list of other suitable salts may be found in for example "Remington's Pharmaceutical Sciences", 20th Ed., Mack Publishing Company, Easton, Pa., (1985); and "Handbook of Pharmaceutical Salts:Properties, Selection, and Use", Stahl and Wermuth (Wiley-VCH, Weinheim, Germany, 2002).

The term "metabolite" used herein refers to the product obtained in vivo by metabolism of a specific compound or the salt thereof. A metabolite of a compound can be identified using technologies in the common knowledge of the art, the activity thereof can be characterized using experimental methods described in the invention. Such product may be obtained from the administrated compound by methods like oxidation, reduction, hydrolysis, amidation, de-amidation, esterification, de-esterification, enzyme cleavage, etc. Accordingly, the metabolite of the compound of the invention is encompassed by the invention, for example the metabolite produced by sufficiently contacting the compound of the invention with a mammal for a period of time. It is understood that, the stereisomer, tautomer, nitrogen oxide, solvate (e.g. hydrate), metabolite, and the like, of the compound of the invention or the salt thereof, is also encompassed by the invention. These forms are preferably pharmaceutically acceptable.

The term "prodrug" used in the invention refers to a compound that can be transformed in vivo into the compound of Formula I. Such transformation is affected by hydrolysis of the drug precursor in blood or the enzymic transformation of the drug precursor in blood or tissue to the parent molecule. The following literature may be the reference for a detailed discussion of the drug precursor: Higuchi et al., *Pro-drugs as Novel Delivery Systems*, Vol. 14, A.C.S. Symposium Series; Roche et al., ed., *Bioreversible Carriers in Drug Design*, American Pharmaceutical Association and Pergamon Press, 1987; Rautio et al., *Prodrugs: Design and Clinical Applications*, Nature Reviews Drug Discovery, 2008, 7, 255-270, and Hecker et al, *Prodrugs of Phosphates and Phosphonates*, J. Med. Chem., 2008, 51, 2328-2345. The disclosure of each literature is incorporated herein by reference in its entirety.

Compound of the Invention

Provided is a compound of Formula I or a pharmaceutically acceptable salt or prodrug thereof,

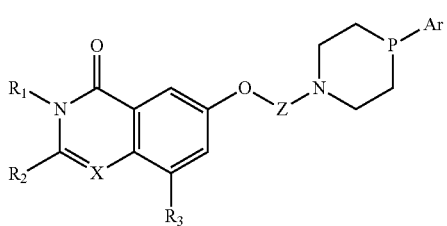

I wherein,

X is C, O, N or NH;

Z is $-(CH_2)_n-$, which is unsubstituted or substituted by one or more substituents selected from the group consisting of alkyl, cyano, hydroxy and halogen, n is an integer of 2~7;

$R_1$ or $R_2$ are each independently hydrogen, linear or branched alkyl containing 1~5 carbon atoms, wherein the alkyl is optionally substituted by one or more substituents selected from the group consisting of alkyl, cyano, hydroxy and halogen;

$R_3$ is hydrogen, halogen or linear or branched alkyl containing 1~5 carbon atoms, wherein the alkyl is optionally substituted by one or more substituents selected from the group consisting of alkyl, cyano, hydroxy and halogen;

P is CH or N;

Ar is a group selected from the group consisting of formula II-VII:

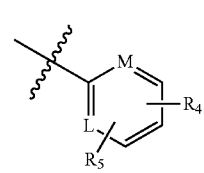

II

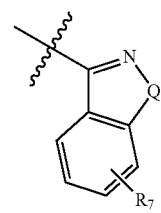

III

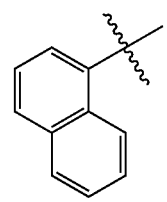

IV

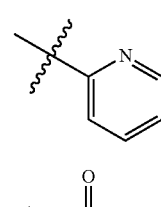

V

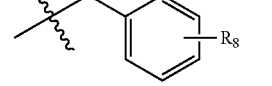

VI

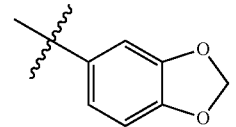

VII

L and M are independently CH or N;

Q is O or S;

$R_4$, $R_5$, $R_6$, $R_7$ or $R_8$ are each independently hydrogen, halogen, linear or branched alkyl containing 1~5 carbon atoms, or alkoxyl containing 1~5 carbon atoms, wherein the alkyl and alkoxyl are optionally substituted by one or more substituents selected from the group consisting of alkyl, cyano, hydroxy and halogen.

In an embodiment, $R_1$ and $R_2$ in formula I are each independently hydrogen, methyl, ethyl, propyl, n-butyl, iso-butyl, trifluoromethyl, trifluoroethyl or trifluoropropyl.

In another embodiment, $R_3$ in formula I is hydrogen, fluorine, chlorine, bromine, iodine, methyl, ethyl, propyl, n-butyl or iso-butyl.

In another embodiment, $R_4$, $R_5$ and $R_8$ in formula I are each independently hydrogen, halogenated $C_{1-5}$ alkyl, methoxyl, ethoxyl, propoxy, chlorine, fluorine or bromine.

In a preferable embodiment, the halogenated $C_{1-5}$ alkyl is trifluoromethyl, trifluoroethyl, trifluoropropyl or trifluorobutyl.

In an embodiment, the halogen is fluorine, chlorine, bromine or iodine.

In an preferable embodiment of the invention,

X is C, O, N or NH;

Z is $-(CH_2)_n-$, which is unsubstituted or substituted by one or more hydroxy, n is an integer of 2~5;

$R_1$ is hydrogen, methyl or ethyl;

$R_2$ is hydrogen, methyl or ethyl;

$R_3$ is hydrogen, methyl or fluorine.

In particular, provided is at least one of the following compounds or a pharmaceutically acceptable stereisomer, tautomer, nitrogen oxide, solvate (e.g. hydrate), metabolite, salt or prodrug thereof:

1

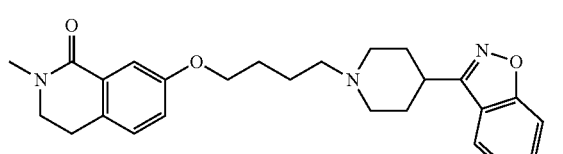

2

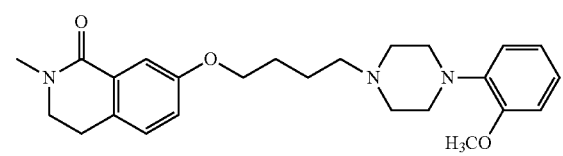

3

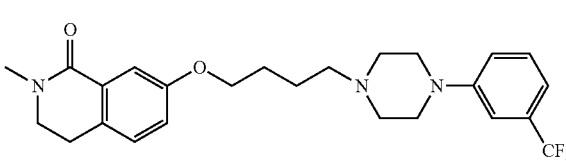

4

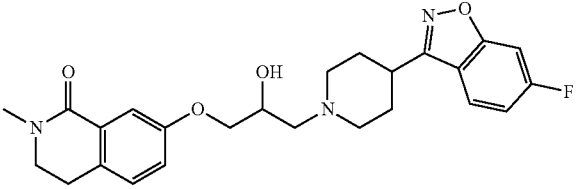

5

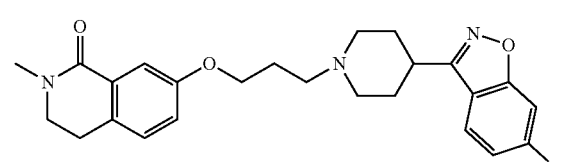

6

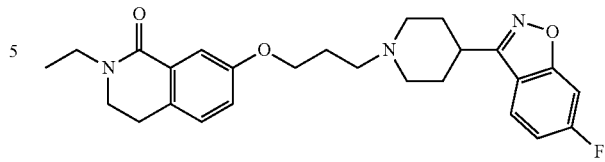

7

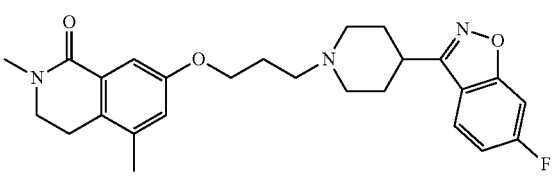

8

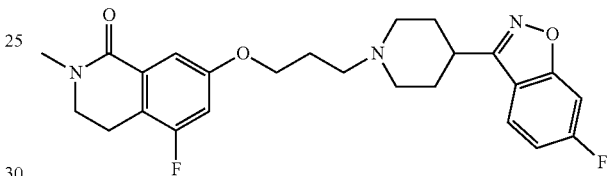

9

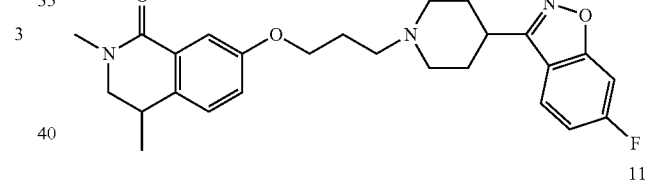

10

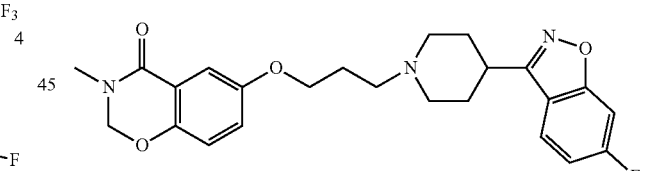

11

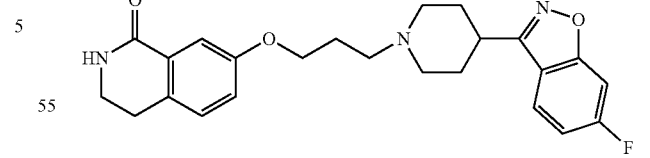

12

13

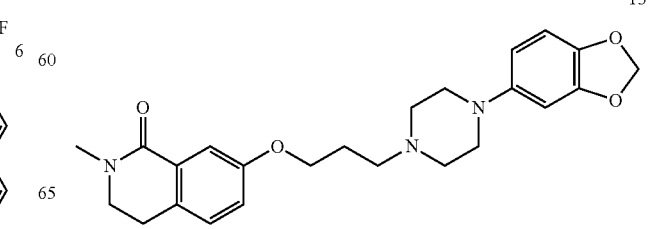

14
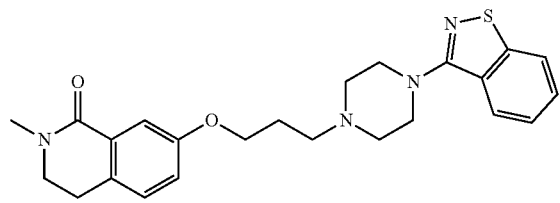
15
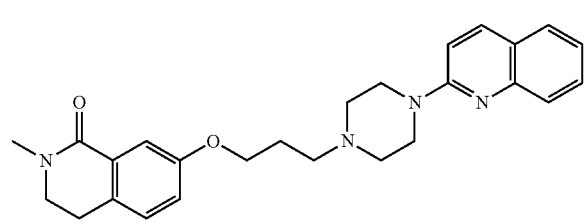
16
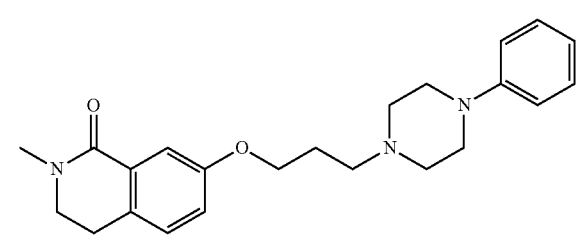
17
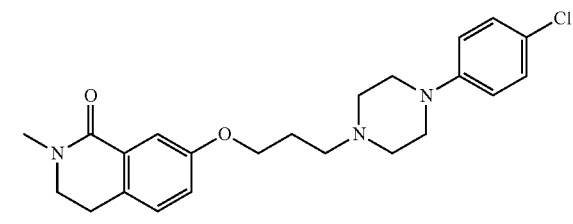
18
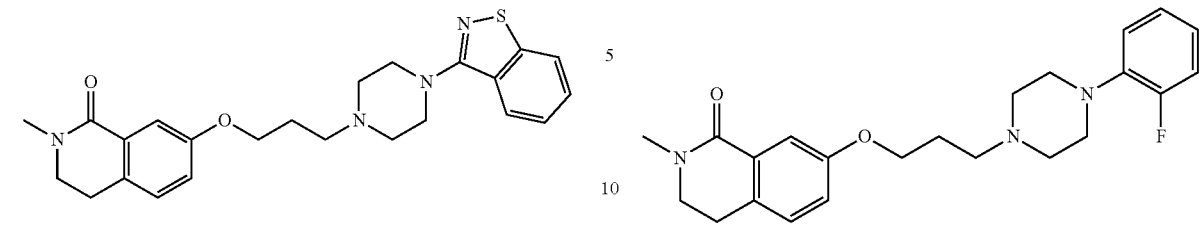
19
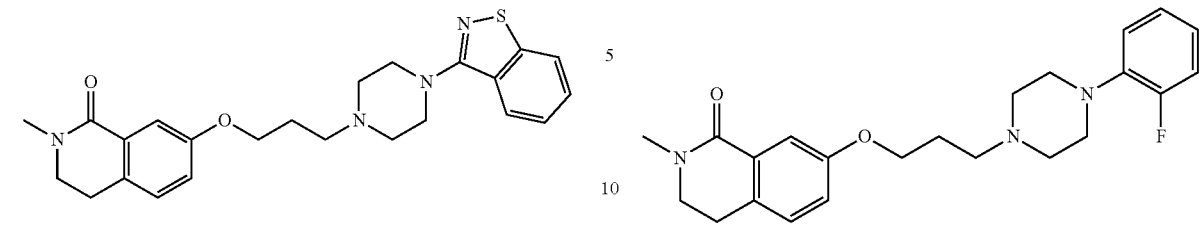
20
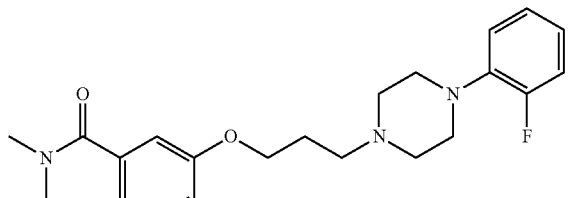
21
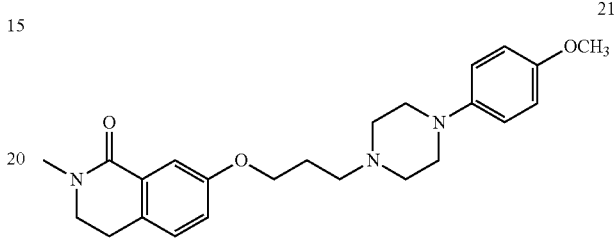
22
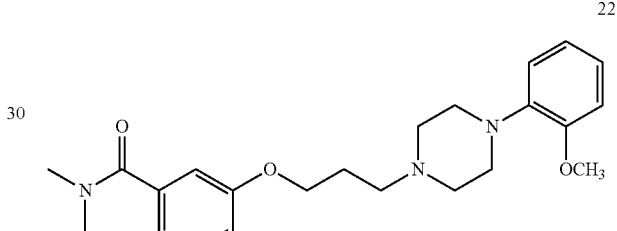
23
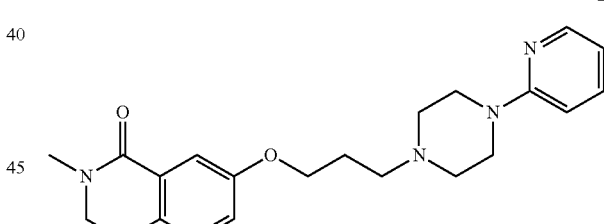
24
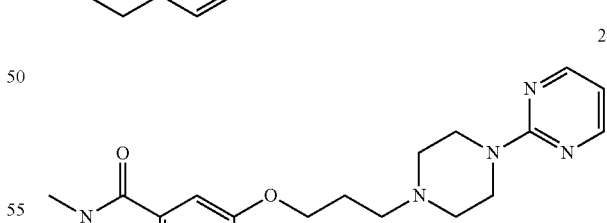
25
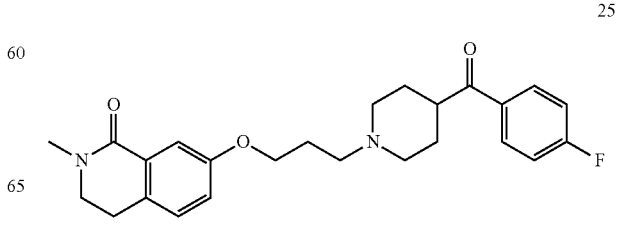

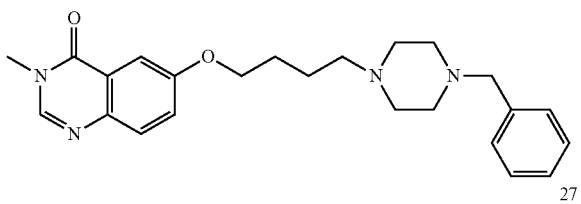

26

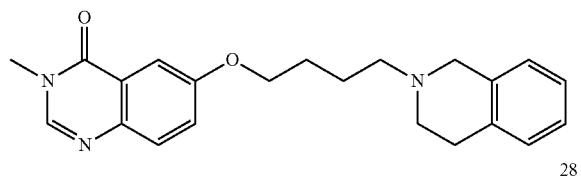

27

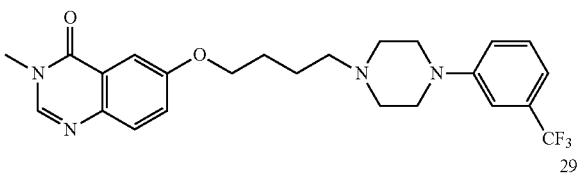

28

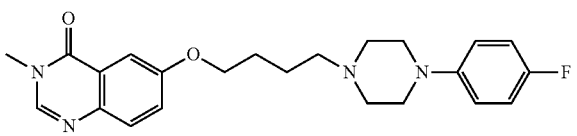

29

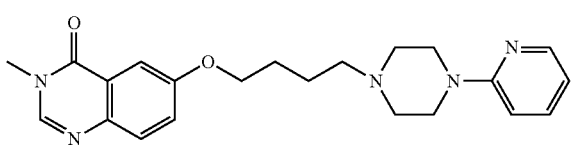

30

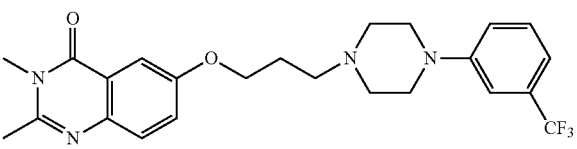

31

Pharmaceutical Composition and Administration

Provided is a pharmaceutical composition, which comprises a compound of formula I or a pharmaceutically acceptable salt, and a pharmaceutically acceptable excipient, carrier, adjuvant, solvent or the combination thereof.

The pharmaceutical composition according to the invention can be administered through any suitable route, for example, oral administration in capsule form, parenteral administration in the form of injection, topical application in the form of ointment or lotion, rectal application in the form of suppository, and transdermal administration in the form of patch delivery system.

According to an embodiment of the invention, an effective amount of a compound of the invention or a pharmaceutically acceptable salt thereof may be orally administered together with carriers such as inert diluent. Examples of suitable pharmaceutically acceptable carriers include, but are not limited to, inert solid fillers or diluents and sterile aqueous or organic solutions. According to some embodiments of the invention, the compound of the invention or a pharmaceutically acceptable salt thereof may be enclosed in a gelatin capsule or compressed into a tablet. For the purpose of oral treatment, the compound of the invention or the pharmaceutically acceptable salt thereof may be used with excipients, and in the form of for example tablets, lozenges, capsules, suspensions, syrups and the like.

The compounds of the invention can be combined with suitable solid or liquid carriers or diluents to form capsules, tablets, pills, powders, syrups, solutions and the like. Such forms like tablets, pills, capsules etc., may contain from about 0.01 to about 99 wt % of the active ingredient (e.g., the compound of the invention or a pharmaceutically acceptable salt thereof) and binders such as gelatin, corn starch, acacia; excipients such as calcium hydrogen phosphate; disintegrants such as corn starch, potato starch or alginic acid; lubricants such as magnesium stearate; and sweeteners such as sucrose, lactose. When capsules are used, liquid carriers may also be contained, for example, fats and oils. When used for parenteral administration, the compound of the invention or a pharmaceutically acceptable salt thereof may be combined with sterile aqueous or organic medium to form an injectable solution or suspension.

According to an embodiment of the invention, the formulation may contain at least 0.5 wt % of a compound of the invention or a pharmaceutically acceptable salt thereof, but according to the particular variation of the dosage form, a range from about 4 wt % to about 70 wt % may also be advantageous. A preferable oral unit dose of the invention may contain 1.0 to 300 milligrams of a compound of the invention or a pharmaceutically acceptable salt thereof.

The pharmaceutical composition of the invention can provide about 0.01 to 1000 mg of active ingredient in each unit dose. The amount of the compound of the invention depends on the type and severity of the disease or disorder and also on the characteristics of the subject, such as general health, age, gender, weight, and drug resistance. A person skilled in the art can determine the appropriate dosage based on these or other factors. The effective dose of a central nervous system drug commonly used is well known to a person skilled in the art. The total daily dose is usually about 0.05 to 2000 mg.

Beneficial Effect

In vitro receptor binding assay indicates that the compound of the invention has high affinities for $D_2$, $5HT_{1A}$ and $5HT_{2A}$, thereby has anti-neuropsychiatric disease activity, i.e. has effect on the treatment or prevention of neuropsychiatric disease, in particular schizophrenia. Meanwhile, the compound of the invention has low affinities for $H_1$ (lowers the risk of obesity, and can increase the efficacy of the drug (e.g. improving the negative symptoms), reduce side effects (e.g. EPS, increase of prolactine, bodyweight gain and prolonged QI interval). Preferably, the compound of the invention has high affinity for $5HT_7$ receptor and may be beneficial for improving the cognitive disorders.

Animal assays show that the compound of the invention can not only significantly improve the MK-801 induced high activity, but also effectively improve the apomorphine induced clambering symptoms without causing EPS at effective dosage, indicating that they have notable anti-schizophrenia effects. Since these in vitro targets and in vivo pharmacological models are closely relevant to nervous system diseases caused by dopamine dysfunction, in particular schizophrenia, it is suggested that the compound of the invention has effect on the treatment or prevention of neuropsychiatric disease, in particular schizophrenia.

General Synthetic Scheme

When X is C in the compound of the invention, the general synthetic method may include reacting 4-methoxy-phenylethylamine with ethyl chloroformate, which is selfcyclized in the presence of methanesulfonic acid and diphosphorus pentoxide, subjecting N at amide to methylation with iodomethane, demethylating the methyl of methoxyl using hydrobromic acid aqueous solution, then reacting with 1,3-dibromopropane or 1,4-dibromobutane respectively, and finally reacting with corresponding piperazine or piperidine to give the target product. The specific reaction route is as follows:

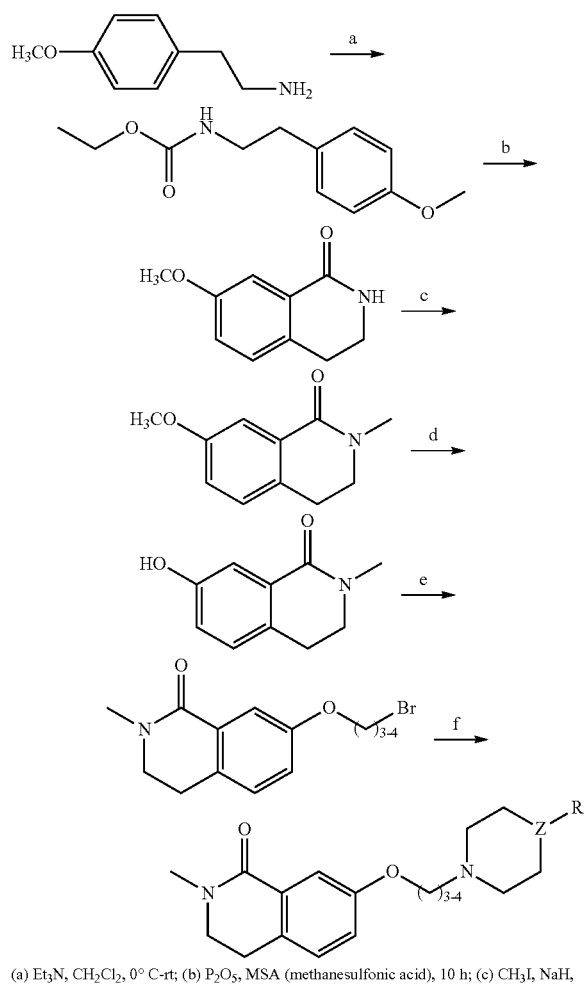

(a) Et₃N, CH₂Cl₂, 0° C-rt; (b) P₂O₅, MSA (methanesulfonic acid), 10 h; (c) CH₃I, NaH, DMF; (d) HBr/H₂O; (e) K₂CO₃, acetone; (f) K₂CO₃, CH₃CN.

When X is N (Y can be N in the scheme) in the compound of the invention, the generic synthetic method may include reacting 2-amino-5-hydroxybenzoic acid with acetic anhydride and N-methyl formamide respectively to give a product, then reacting with 1,3-dibromopropane or 1,4-dibromobutane respectively, and finally reacting with corresponding piperazine or piperidine to obtain the target product. The specific reaction route is as follows:

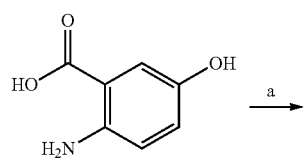

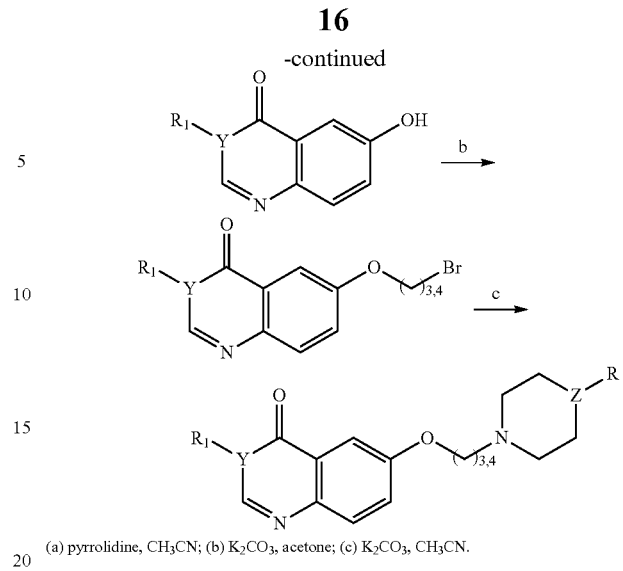

(a) pyrrolidine, CH₃CN; (b) K₂CO₃, acetone; (c) K₂CO₃, CH₃CN.

SYNTHETIC EXAMPLES

The specific examples of the invention are described below. The examples described below are exemplary, provided for the purpose of illustration to the invention only rather than limitation thereto. Unless defined otherwise, proportion and percentage are calculated based on weight herein. The following synthetic Examples 1-31 are all conducted based on the general method as above. The compounds prepared in each Example are listed in Table 1.

Example 1

7-(4-(4-(6-fluorobenzo[d]isoxazol-3-yl)piperidin-1-yl)butoxy)-2-methyl-3,4-dihydroisoquinolin-1(2H)-one (1)

(1) 4-methoxyphenylethylamine (0.1 mol) was dissolved in dichloromethane (300 ml), the mixture was cooled to 0° C. in ice bath, then triethylamine (20 ml) was added, and then ethyl chloroformate (0.15 mmol) was added slowly dropwise. After addition, the reaction was conducted at room temperature for 12 hours. After the reaction was completed, the reaction solution was washed with water and 10% diluted hydrochloric acid solution. The organic layer was dried over anhydrous magnesium sulfate. The solvent was removed by evaporation under reduced pressure. The residue was washed with petroleum ether and dried to give 20.3 g of yellow oil. Yield: 91%.

MS (ESI) m/z 223.3 ([M+H]⁺)

(2) Diphosphorus pentoxide (0.2 mol) was dissolved in methanesulfonic acid (200 ml), then the yellow oil (0.1 mol) prepared in step (1) was added in batches. The reaction was conducted at 140° C. After the reaction was completed, the reaction solution was poured into ice water (500 ml) for termination. The mixture was extracted with dichloromethane. The organic layer was washed with saturated sodium carbonate, dried over anhydrous magnesium sulfate. The solvent was removed by evaporation under reduced pressure. The residue was applied to column chromatography (eluent: petroleum ether:ethyl acetate=10:1) to give 12.9 g of brownish oil. Yield: 73%.

MS (ESI) m/z 177.1 ([M+H]⁺)

(3) 0.2 mol sodium hydroxide was dissolved in 200 ml N,N-dimethyl formamide, then the oil (0.1 mol) prepared in step (2) was added, The reaction was stirred in ice bath for 0.5 hour, and then iodomethane (0.15 mol) was slowly added dropwise. After the addition was completed, the reaction was conducted at room temperature for 10 hours. After the reaction was completed, the reaction solution was poured into 1 L ice water to terminate the reaction. Extraction with ethyl acetate was conducted. The organic layer was washed with saturated saline solution, dried over anhydrous magnesium sulfate. The solvent was removed by rotary evaporation to give 17.8 g of brown solid. Yield: 93%.

MS (ESI) m/z 191.1 ([M+H]$^+$)

(4) The brown solid (0.1 mmol) prepared in step (3) was reacted in 48% hydrobromic acid aqueous solution (100 ml) at 100° C. for 10 hours. After the reaction was completed, water was added to terminate the reaction. The mixture was extracted with ethyl acetate and washed with saturated sodium bicarbonate solution. The organic layer was dried over anhydrous magnesium sulfate. The solvent was removed by rotary evaporation. The residue was applied to column chromatography (eluent: petroleum ether:ethyl acetate=1:1) to give 8.1 g of brownish solid. Yield: 46%.

MS (ESI) m/z 177.2 ([M+H]$^+$)

(5) To acetone (200 ml) was added the brownish solid (0.1 mmol) prepared in step (4), 1,4-dibromobutane (0.12 mmol) and potassium carbonate (0.3 mmol). The reaction was refluxed for 12 hours. After the reaction was completed, suction filtration was conducted to give organic solution which was then evaporated to dryness under reduced pressure. The residue was applied to column chromatography (eluent: petroleum ether:ethyl acetate=10:1 to give 26.4 g of light yellow oil. Yield: 89%.

MS (ESI) m/z 297.0 ([M+H]$^+$)

(6) To acetonitrile (50 ml) was added the light yellow oil (2 mmol) prepared in step (5), 6-fluoro-3-(piperidin-4-yl) benzo[d]isoxazole (2 mmol) and potassium carbonate (6 mmol). The reaction was refluxed for 10 hours. After the reaction was completed, suction filtration was conducted to give organic solution. Acetonitrile was evaporated to dryness, The residue was applied to column chromatography (eluent: CH$_2$Cl$_2$:methanol=10:1 to give 0.38 g of yellow oil. Yield: 87%.

MS (ESI) m/z 437.2 ([M+H]$^+$). The structural formula is shown as No. (1) in Table 1.

$^1$H-NMR (600 MHz, CDCl$_3$) δ 1.74-1.87 (m, 8H), 2.05-2.19 (m, 6H), 2.48 (t, 2H, J=12 Hz), 2.93 (t, 2H, J=12 Hz), 3.07-3.11 (m, 2H), 3.16 (s, 3H), 3.55 (t, 2H, J=12 Hz), 4.06 (t, 2H, J=6 Hz), 6.96-6.98 (m, 1H), 7.04-7.09 (m, 2H), 7.24-7.26 (m, 1H), 7.61 (d, 1H, J=6 Hz), 7.73-7.74 (m, 1H). MS (ESI) m/z 452.2 ([M+H]$^+$).

$^1$H-NMR (600 MHz, CDCl$_3$) δ 1.74-1.86 (m, 8H), 2.55-2.56 (m, 2H), 2.71-2.73 (m, 2H), 2.93 (t, 2H, J=12 Hz), 3.10 (t, 2H, J=12 Hz), 3.14 (s, 3H), 3.53 (t, 2H, J=12 Hz), 4.03 (t, 2H, J=6 Hz), 6.94-6.97 (m, 2H), 7.05-7.16 (m, 3H), 7.58 (d, 1H, J=6 Hz). MS (ESI) m/z 462.1 ([M+H]$^+$).

Example 2

7-(4-(4-(2-methoxyphenyl)piperazin-1-yl)butoxy)-2-methyl-3,4-dihydroisoquinolin-1(2H)-one (2)

The target compound was prepared according to the method of Example 1, using 1-(2-methoxyphenyl)piperazine instead of 6-fluoro-3-(piperidin-4-yl)benzo[d]isoxazole as raw material. The structural formula is shown as No. (2) in Table 1.

$^1$H-NMR (600 MHz, CDCl$_3$) δ 1.72-1.86 (m, 4H), 2.50 (t, 2H, J=12 Hz), 2.69-2.70 (m, 3H), 2.94 (t, 2H, J=12 Hz), 3.12-3.16 (m, 2H), 3.18 (s, 3H), 3.54 (t, 2H, J=12 Hz), 3.87 (s, 3H), 4.05 (t, 2H, J=6 Hz), 6.86-6.88 (m, 1H), 6.91-7.07 (m, 5H), 7.61 (d, 1H, J=6 Hz). MS (ESI) m/z 424.3 ([M+H]$^+$).

Example 3

2-methyl-7-(4-(4-(3-(trifluoromethyl)phenyl)piperazin-1-yl)butoxy)-3,4-dihydroisoquinolin-1 (2H)-one (3)

The target compound was prepared according to the method of Example 1, using 1-(3-(trifluoromethyl)phenyl) instead of 6-fluoro-3-(piperidin-4-yl)benzo[d]isoxazole as raw material. The structural formula is shown as No. (3) in Table 1.

$^1$H-NMR (600 MHz, CDCl$_3$) δ 1.73-1.88 (m, 4H), 2.21-2.22 (m, 2H), 2.50 (t, 2H, J=12 Hz), 2.64-2.66 (m, 3H), 2.94 (t, 2H, J=12 Hz), 3.18 (s, 3H), 3.26-3.28 (m, 3H), 3.55 (t, 2H, J=12 Hz), 4.06 (t, 2H, J=6 Hz), 6.96-6.98 (m, 1H), 7.06-7.10 (m, 3H), 7.12-7.14 (m, 1H), 7.34-7.36 (m, 1H), 7.61 (d, 1H, J=6 Hz). MS (ESI) m/z 462.2 ([M+H]$^+$).

Example 4

7-(3-(4-(6-fluorobenzo[d]isoxazol-3-yl)piperidin-1-yl)-2-hydroxypropoxy)-2-methyl-3,4-dihydroisoquinolin-1(2H)-one (4)

The target compound was prepared according to the method of Example 1, using 2-(chloromethyl)oxirane instead of 1,4-dibromobutane. The structural formula is shown as No. (4) in Table 1.

$^1$H-NMR (600 MHz, CDCl$_3$) δ 1.22-1.25 (m, 2H), 2.09-2.13 (m, 4H), 2.24-2.26 (m, 1H), 2.53-2.65 (m, 3H), 2.94 (t, 2H, J=12 Hz), 3.13-3.17 (m, 4H), 3.19 (s, 3H), 3.21-3.23 (m, 2H), 3.53 (t, 2H, J=12 Hz), 4.05-34.17 (m, 2H), 7.03-7.11 (m, 3H), 7.21-7.26 (m, 1H), 7.64 (d, 1H, J=6 Hz), 7.70-7.72 (m, 1H). MS (ESI) m/z 453.3 ([M+H]$^+$).

Example 5

7-(3-(4-(6-fluorobenzo[d]isoxazol-3-yl)piperidin-1-yl)propoxy)-2-methyl-3,4-dihydroisoquinolin-1(2H)-one (5)

The target compound was prepared according to the method of Example 1, using 1,3-dibromopropane instead of 1,4-dibromobutane. The structural formula is shown as No. (5) in Table 1.

$^1$H-NMR (600 MHz, CDCl$_3$) δ 2.02-2.19 (m, 8H), 2.60 (t, 2H, J=12 Hz), 2.96 (t, 2H, J=12 Hz), 3.09-3.11 (m, 3H), 3.18 (s, 3H), 3.56 (t, 2H, J=12 Hz), 4.11 (t, 2H, J=6 Hz), 6.98-7.00 (m, 1H), 7.06-7.10 (m, 2H), 7.24-7.26 (m, 1H), 7.64 (d, 1H, J=6 Hz), 7.74-7.76 (m, 1H). MS (ESI) m/z 438.2 ([M+H]$^+$).

Example 6

2-methyl-7-(3-(4-(naphthalen-1-yl)piperazin-1-yl)propoxy)-3,4-dihydroisoquinolin-1(2H)-one (6)

The target compound was prepared according to the method of Example 1, using 1,3-dibromopropane instead of 1,4-dibromobutane, and 1-(naphthalen-1-yl)piperazine instead of 6-fluoro-3-(piperidin-4-yl)benzo[d]isoxazole as raw material. The structural formula is shown as No. (6) in Table 1.

¹H-NMR (600 MHz, CDCl₃) δ 1.83-2.07 (m, 4H), 2.58-2.67 (m, 4H), 2.94 (t, 2H, J=12 Hz), 3.16 (s, 3H), 3.21-3.25 (m, 4H), 3.56 (t, 2H, J=12 Hz), 4.10 (t, 2H, J=6 Hz), 6.89-7.10 (m, 6H), 7.27-7.29 (m, 2H), 7.62 (d, 1H, J=6 Hz), 7.74-7.76 (m, 2H). MS (ESI) m/z 430.2 ([M+H]⁺).

Example 7

7-(3-(4-(6-fluorobenzo[d]isoxazol-3-yl)piperidin-1-yl)propoxy)-2-ethyl-3,4-dihydroisoquinolin-1(2H)-one (7)

The target compound was prepared according to the method of Example 1, using iodoethane instead of iodomethane, and 1,3-dibromopropane instead of 1,4-dibromobutane. The structural formula is shown as No. (7) in Table 1.

¹H-NMR (600 MHz, CDCl₃) δ 1.78 (t, 3H, J=12 Hz), 2.01-2.18 (m, 8H), 2.61 (t, 2H, J=12 Hz), 2.95 (t, 2H, J=12 Hz), 3.09-3.14 (m, 5H), 3.56 (t, 2H, J=12 Hz), 4.10 (t, 2H, J=6 Hz), 6.97-7.00 (m, 1H), 7.07-7.10 (m, 2H), 7.24-7.26 (m, 1H), 7.65 (d, 1H, J=6 Hz), 7.75-7.77 (m, 1H). MS (ESI) m/z 453.2 ([M+H]⁺).

Example 8

7-(3-(4-(6-fluorobenzo[d]isoxazol-3-yl)piperidin-1-yl)propoxy)-2,5-dimethyl-3,4-dihydroisoquinolin-1(2H)-one (8)

The target compound was prepared according to the method of Example 1, using 2-methyl-4-methoxyphenylethylamine instead of 4-methoxyphenylethylamine, and 1,3-dibromopropane instead of 1,4-dibromobutane. The structural formula is shown as No. (8) in Table 1.

¹H-NMR (600 MHz, CDCl₃) δ 2.01-2.18 (m, 8H), 2.60 (t, 2H, J=12 Hz), 2.71 (s, 3H), 2.95 (t, 2H, J=12 Hz), 3.09-3.12 (m, 3H), 3.18 (s, 3H), 3.57 (t, 2H, J=12 Hz), 4.10 (t, 2H, J=6 Hz), 6.96-7.00 (m, 1H), 7.07-7.11 (m, 1H), 7.24-7.25 (m, 1H), 7.66 (d, 1H, J=6 Hz), 7.75-7.78 (m, 1H). MS (ESI) m/z 453.1 ([M+H]⁺).

Example 9

5-fluoro-7-(3-(4-(6-fluorobenzo[d]isoxazol-3-yl)piperidin-1-yl)propoxy)-2-methyl-3,4-dihydroisoquinolin-1(2H)-one (9)

The target compound was prepared according to the method of Example 1, using 2-fluoro-4-methoxyphenylethylamine instead of 4-methoxyphenylethylamine, and using 1,3-dibromopropane instead of 1,4-dibromobutane. The structural formula is shown as No. (9) in Table 1

1H-NMR (600 MHz, CDCl3) δ 2.03-2.20 (m, 10H), 2.62 (t, 2H, J=12 Hz), 2.97 (t, 2H, J=12 Hz), 3.09-3.12 (m, 3H), 3.19 (s, 3H), 3.56 (t, 2H, J=12 Hz), 4.12 (t, 2H, J=6 Hz), 7.02-7.11 (m, 2H), 7.24-7.27 (m, 1H), 7.66 (d, 1H, J=6 Hz), 7.75-7.78 (m, 1H). MS (ESI) m/z 453.3 ([M+H]+).

Example 10

7-(3-(4-(6-fluorobenzo[d]isoxazol-3-yl)piperidin-1-yl)propoxy)-2,4-dimethyl-3,4-dihydroisoquinolin-1(2H)-one (10)

The target compound was prepared according to the method of Example 1, using 2-(4-methoxyphenyl)propan-1-amine instead of 4-methoxyphenylethylamine, and 1,3-dibromopropane instead of 1,4-dibromobutane. The structural formula is shown as No. (10) in Table 1.

¹H-NMR (600 MHz, CDCl₃) δ 1.75 (d, 3H, J=8 Hz), 2.01-2.19 (m, 8H), 2.61 (t, 2H, J=12 Hz), 2.95 (t, 2H, J=12 Hz), 3.08-3.10 (m, 3H), 3.17 (s, 3H), 3.55 (t, 2H, J=12 Hz), 4.10 (t, 2H, J=6 Hz), 6.97-7.00 (m, 1H), 7.05-7.10 (m, 2H), 7.24-7.25 (m, 1H), 7.63 (d, 1H, J=6 Hz), 7.74-7.76 (m, 1H). MS (ESI) m/z 438.2 ([M+H]⁺).

Example 11

6-(3-(4-(6-fluorobenzo[d]isoxazol-3-yl)piperidin-1-yl)propoxy)-3-methyl-2H-benzo[e][1,3]oxazin-4(3H)-one (11)

The target compound was prepared according to the method of Example 1, using (4-methoxyphenoxy)methanamine instead of 4-methoxyphenylethylamine, and 1,3-dibromopropane instead of 1,4-dibromobutane. The structural formula is shown as No. (11) in Table 1.

¹H-NMR (600 MHz, CDCl₃) δ 2.01-2.19 (m, 4H), 2.62 (t, 2H, J=12 Hz), 2.96 (t, 2H, J=12 Hz), 3.10-3.12 (m, 3H), 3.19 (s, 3H), 3.57 (t, 2H, J=12 Hz), 4.12 (t, 2H, J=6 Hz), 4.18 (s, 2H), 7.00-7.09 (m, 3H), 7.24-7.27 (m, 1H), 7.66 (d, 1H, J=6 Hz), 7.74-7.77 (m, 1H). MS (ESI) m/z 440.2 ([M+H]⁺).

Example 12

7-(3-(4-(6-fluorobenzo[d]isoxazol-3-yl)piperidin-1-yl)propoxy)-3,4-dihydroisoquinolin-1(2H)-one (12)

The target compound was prepared according to the method of Example 1 without iodomethane, and using 1,3-dibromopropane instead of 1,4-dibromobutane. The structural formula is shown as No. (12) in Table 1.

¹H-NMR (600 MHz, CDCl₃) δ 2.03-2.20 (m, 8H), 2.61 (t, 2H, J=12 Hz), 2.96 (t, 2H, J=12 Hz), 3.08-3.11 (m, 3H), 3.57 (t, 2H, J=12 Hz), 4.10 (t, 2H, J=6 Hz), 6.97-7.00 (m, 1H), 7.07-7.10 (m, 2H), 7.25-7.27 (m, 1H), 7.64 (d, 1H, J=6 Hz), 7.74-7.76 (m, 1H). MS (ESI) m/z 424.3 ([M+H]⁺).

Example 13

7-(3-(4-(benzo[d][1,3]dioxol-5-yl)piperazin-1-yl)propoxy)-2-methyl-3,4-dihydroisoquinolin-1(2H)-one (13)

The target compound was prepared according to the method of Example 1, using 1,3-dibromopropane instead of 1,4-dibromobutane, and 1-(benzo[d][1,3]dioxol-5-yl)piperazine instead of 6-fluoro-3-(piperidin-4-yl)benzo[d]isoxazole as raw material. The structural formula is shown as No. (13) in Table 1.

¹H-NMR (600 MHz, CDCl₃) δ 1.80-2.02 (m, 8H), 2.57 (t, 2H, J=12 Hz), 2.96 (t, 2H, J=12 Hz), 3.09-3.15 (m, 2H), 3.19 (s, 3H), 3.58 (t, 2H, J=12 Hz), 4.12 (t, 2H, J=6 Hz), 4.20 (s, 2H), 6.98-7.00 (m, 1H), 7.06-7.15 (m, 3H), 7.63 (d, 1H, J=6 Hz), 7.98-8.02 (m, 2H). MS (ESI) m/z 424.3 ([M+H]⁺).

Example 14

7-(3-(4-(benzo[d]isothiazol-3-yl)piperazin-1-yl)propoxy)-2-methyl-3,4-dihydroisoquinolin-1(2H)-one (14)

The target compound was prepared according to the method of Example 1, using 1,3-dibromopropane instead of 1,4-dibromobutane, and 3-(piperazin-1-yl)benzo[d]isothiazole instead of 6-fluoro-3-(piperidin-4-yl)benzo[d]isoxazole as raw material. The structural formula is shown as No. (14) in Table 1.

$^1$H-NMR (600 MHz, CDCl$_3$) δ 2.01-2.18 (m, 6H), 2.61 (t, 2H, J=12 Hz), 2.97 (t, 2H, J=12 Hz), 3.09-3.13 (m, 4H), 3.18 (s, 3H), 3.57 (t, 2H, J=12 Hz), 4.11 (t, 2H, J=6 Hz), 6.97-7.00 (m, 2H), 7.07-7.10 (m, 2H), 7.23-7.26 (m, 1H), 7.63 (d, 1H, J=6 Hz), 7.75-7.77 (m, 1H). MS (ESI) m/z 438.2 ([M+H]$^+$).

Example 15

7-(3-(4-(quinolin-2-yl)piperazin-1-yl)propoxy)-2-methyl-3,4-dihydroisoquinolin-1(2H)-one (15)

The target compound was prepared according to the method of Example 1, using 1,3-dibromopropane instead of 1,4-dibromobutane, and 1 (quinolin-2-yl)-piperazine instead of 6-fluoro-3-(piperidin-4-yl)benzo[d]isoxazole as raw material. The structural formula is shown as No. (15) in Table 1.

1H-NMR (600 MHz, CDCl3) δ 1.81-2.06 (m, 4H), 2.59-2.65 (m, 4H), 2.94 (t, 2H, J=12 Hz), 3.18 (s, 3H), 3.21-3.25 (m, 4H), 3.57 (t, 2H, J=12 Hz), 4.11 (t, 2H, J=6 Hz), 6.56-6.58 (m, 1H), 6.85-7.10 (m, 5H), 7.26-7.27 (m, 1H), 7.63 (d, 1H, J=6 Hz), 7.74-7.76 (m, 2H). MS (ESI) m/z 431.2 ([M+H]+).

Example 16

2-methyl-7-(3-(4-phenylpiperazin-1-yl)propoxy)-3,4-dihydroisoquinolin-1(2H)-one (16)

The target compound was prepared according to the method of Example 1, using 1,3-dibromopropane instead of 1,4-dibromobutane, and 1-phenylpiperazine instead of 6-fluoro-3-(piperidin-4-yl)benzo[d]isoxazole as raw material. The structural formula is shown as No. (16) in Table 1.

$^1$H-NMR (600 MHz, CDCl$_3$) δ 1.81-2.07 (m, 4H), 2.59-2.67 (m, 4H), 2.95 (t, 2H, J=12 Hz), 3.17 (s, 3H), 3.22-3.25 (m, 4H), 3.56 (t, 2H, J=12 Hz), 4.11 (t, 2H, J=6 Hz), 6.85-7.10 (m, 4H), 7.26-7.27 (m, 1H), 7.63 (d, 1H, J=6 Hz), 7.74-7.76 (m, 2H). MS (ESI) m/z 380.2 ([M+H]$^+$).

Example 17

7-(3-(4-(4-chlorophenyl)piperazin-1-yl)propoxy)-2-methyl-3,4-dihydroisoquinolin-1(2H)-one (17)

The target compound was prepared according to the method of Example 1, using 1,3-dibromopropane instead of 1,4-dibromobutane, and 1-(4-chlorophenyl)piperazine instead of 6-fluoro-3-(piperidin-4-yl)benzo[d]isoxazole as raw material. The structural formula is shown as No. (17) in Table 1.

$^1$H-NMR (600 MHz, CDCl$_3$) δ 2.03-2.08 (m, 2H), 2.61-2.69 (m, 6H), 2.96 (t, 2H, J=12 Hz), 3.09-3.12 (m, 4H), 3.19 (s, 3H), 3.56 (t, 2H, J=12 Hz), 4.10 (t, 2H, J=6 Hz), 6.97-7.00 (m, 1H), 7.06-7.10 (m, 4H), 7.39-7.42 (m, 2H), 7.65 (d, 1H, J=6 Hz). MS (ESI) m/z 414.2 ([M+H]$^+$).

Example 18

7-(3-(4-(2-chlorophenyl)piperazin-1-yl)propoxy)-2-methyl-3,4-dihydroisoquinolin-1(2H)-one (18)

The target compound was prepared according to the method of Example 1, using 1,3-dibromopropane instead of 1,4-dibromobutane, and 1-(2-chlorophenyl)piperazine instead of 6-fluoro-3-(piperidin-4-yl)benzo[d]isoxazole as raw material. The structural formula is shown as No. (18) in Table 1.

$^1$H-NMR (600 MHz, CDCl$_3$) δ 2.02-2.07 (m, 2H), 2.60-2.69 (m, 6H), 2.95 (t, 2H, J=12 Hz), 3.09-3.11 (m, 4H), 3.18 (s, 3H), 3.55 (t, 2H, J=12 Hz), 4.11 (t, 2H, J=6 Hz), 6.96-7.00 (m, 1H), 7.06-7.10 (m, 2H), 7.22-7.26 (m, 1H), 7.35-7.38 (m, 1H), 7.63 (d, 1H, J=6 Hz). MS (ESI) m/z 414.3 ([M+H]$^+$).

Example 19

7-(3-(4-(4-fluorophenyl)piperazin-1-yl)propoxy)-2-methyl-3,4-dihydroisoquinolin-1(2H)-one (19)

The target compound was prepared according to the method of Example 1, using 1,3-dibromopropane instead of 1,4-dibromobutane, and 1-(4-fluorophenyl)piperazine instead of 6-fluoro-3-(piperidin-4-yl)benzo[d]isoxazole as raw material. The structural formula is shown as No. (19) in Table 1.

$^1$H-NMR (600 MHz, CDCl$_3$) δ 2.04-2.08 (m, 2H), 2.61-2.69 (m, 6H), 2.97 (t, 2H, J=12 Hz), 3.10-3.12 (m, 4H), 3.19 (s, 3H), 3.57 (t, 2H, J=12 Hz), 4.12 (t, 2H, J=6 Hz), 6.99-7.02 (m, 1H), 7.07-7.10 (m, 3H), 7.40-7.44 (m, 2H), 7.66 (d, 1H, J=6 Hz). MS (ESI) m/z 398.2 ([M+H]$^+$).

Example 20

7-(3-(4-(2-fluorophenyl)piperazin-1-yl)propoxy)-2-methyl-3,4-dihydroisoquinolin-1(2H)-one (20)

The target compound was prepared according to the method of Example 1, using 1,3-dibromopropane instead of 1,4-dibromobutane, and 1-(2-fluorophenyl)piperazine instead of 6-fluoro-3-(piperidin-4-yl)benzo[d]isoxazole as raw material. The structural formula is shown as No. (20) in Table 1.

$^1$H-NMR (600 MHz, CDCl$_3$) δ 1.73-2.07 (m, 4H), 2.60-2.69 (m, 6H), 2.96 (t, 2H, J=12 Hz), 3.13-3.15 (m, 4H), 3.17 (s, 3H), 3.57 (t, 2H, J=12 Hz), 4.11 (t, 2H, J=6 Hz), 6.947.10 (m, 6H), 7.63 (d, 1H, J=6 Hz). MS (ESI) m/z 398.2 ([M+H]$^+$).

Example 21

7-(3-(4-(4-methoxyphenyl)piperazin-1-yl)propoxy)-2-methyl-3,4-dihydroisoquinolin-1(2H)-one (21)

The target compound was prepared according to the method of Example 1, using 1,3-dibromopropane instead of 1,4-dibromobutane, and 1-(4-methoxyphenyl)piperazine instead of 6-fluoro-3-(piperidin-4-yl)benzo[d]isoxazole as raw material. The structural formula is shown as No. (21) in Table 1.

$^1$H-NMR (600 MHz, CDCl$_3$) δ 1.75-2.05 (m, 4H), 2.61-2.69 (m, 6H), 2.95 (t, 2H, J=12 Hz), 3.11-3.14 (m, 4H), 3.17 (s, 3H), 3.56 (t, 2H, J=12 Hz), 3.79 (s, 3H), 4.11 (t, 2H, J=6 Hz), 6.85-7.00 (m, 5H), 7.08-7.10 (m, 1H), 7.63 (d, 1H, J=6 Hz). MS (ESI) m/z 410.2 ([M+H]$^+$).

Example 22

7-(3-(4-(2-methoxyphenyl)piperazin-1-yl)propoxy)-2-methyl-3,4-dihydroisoquinolin-1(2H)-one (22)

The target compound was prepared according to the method of Example 1, using 1,3-dibromopropane instead of 1,4-dibromobutane, and 1-(2-methoxyphenyl)piperazine instead of 6-fluoro-3-(piperidin-4-yl)benzo[d]isoxazole as raw material. The structural formula is shown as No. (22) in Table 1.

$^1$H-NMR (600 MHz, CDCl$_3$) δ 1.07-2.05 (m, 4H), 2.61-2.68 (m, 6H), 2.96 (t, 2H, J=12 Hz), 3.13-3.15 (m, 4H), 3.18 (s, 3H), 3.57 (t, 2H, J=12 Hz), 3.78 (s, 3H), 4.11 (t, 2H, J=6 Hz), 6.88-7.10 (m, 6H), 7.64 (d, 1H, J=6 Hz). MS (ESI) m/z 410.3 ([M+H]$^+$).

Example 23

2-methyl-7-(3-(4-(pyridin-2-yl)piperazin-1-yl)propoxy)-3,4-dihydroisoquinolin-1(2H)-one (23)

The target compound was prepared according to the method of Example 1, using 1,3-dibromopropane instead of 1,4-dibromobutane, and 1-(pyridin-2-yl)piperazine instead of 6-fluoro-3-(piperidin-4-yl)benzo[d]isoxazole as raw material. The structural formula is shown as No. (23) in Table 1.

$^1$H-NMR (600 MHz, CDCl$_3$) δ 1.98-2.03 (m, 2H), 2.54-2.67 (m, 6H), 2.91 (t, 2H, J=12 Hz), 3.13 (s, 3H), 3.50-3.55 (m, 6H), 4.08 (t, 2H, J=6 Hz), 6.58-6.84 (m, 2H), 6.94-7.06 (m, 2H), 7.44-7.46 (m, 1H), 7.60 (d, 1H, J=6 Hz), 8.16-8.18 (m, 1H). MS (ESI) m/z 381.2 ([M+H]$^+$).

Example 24

2-methyl-7-(3-(4-(pyrimidin-2-yl)piperazin-1-yl)propoxy)-3,4-dihydroisoquinolin-1(2H)-one (24)

The target compound was prepared according to the method of Example 1, using 1,3-dibromopropane instead of 1,4-dibromobutane, and 2-(piperazin-1-yl)pyrimidine instead of 6-fluoro-3-(piperidin-4-yl)benzo[d]isoxazole as raw material. The structural formula is shown as No. (24) in Table 1.

$^1$H-NMR (600 MHz, CDCl$_3$) δ 1.81-2.05 (m, 4H), 2.59-2.67 (m, 4H), 2.96 (t, 2H, J=12 Hz), 3.17 (s, 3H), 3.54 (t, 2H, J=12 Hz), 3.84-3.88 (m, 4H), 4.11 (t, 2H, J=6 Hz), 6.48-6.51 (m, 1H), 6.97-7.10 (m, 2H), 7.63 (d, 1H, J=6 Hz), 8.32 (d, 2H, J=6 Hz). MS (ESI) m/z 382.3 ([M+H]$^+$).

Example 25

7-(3-(4-(4-fluorobenzoyl)piperidin-1-yl)propoxy)-2-methyl-3,4-dihydroisoquinolin-1(2H)-one (25)

The target compound was prepared according to the method of Example 1, using 1,3-dibromopropane instead of 1,4-dibromobutane, and (4-fluorophenyl)(piperidin-4-yl)methanone instead of 6-fluoro-3-(piperidin-4-yl)benzo[d]isoxazole as raw material. The structural formula is shown as No. (25) in Table 1.

$^1$H-NMR (600 MHz, CDCl$_3$) δ 1.82-2.02 (m, 6H), 2.10-2.17 (m, 2H), 2.55 (t, 2H, J=12 Hz), 2.92 (t, 2H, J=12 Hz), 3.00-3.05 (m, 2H), 3.17 (s, 3H), 3.53 (t, 2H, J=12 Hz), 4.06 (t, 2H, J=6 Hz), 6.94-6.97 (m, 1H), 7.05-7.15 (m, 3H), 7.60 (d, 1H, J=6 Hz), 7.95-7.98 (m, 2H). MS (ESI) m/z 425.3 ([M+H]$^+$).

Example 26

6-(4-(4-benzylpiperazin-1-yl)butoxy)-3-methylquinazolin-4(3H)-one (26)

(1) 2-amino-5-hydroxybenzoic acid (0.1 mol) and N-methylformamide were reacted at 160° C. for 10 hours. After the reaction was completed, ice water was used to terminate the reaction. Extraction with ethyl acetate was conducted. The organic layer was dried over anhydrous magnesium sulfate. The solvent was removed by evaporation under reduced pressure. The residue was applied to column chromatography (eluent: petroleum ether:ethyl acetate=1:1) to give 13 g of brown solid. Yield: 74%.

MS (ESI) m/z 176.1 ([M+H]$^+$).

(2) The brown solid (0.1 mmol) prepared in step (1), 1,4-dibromobutane (0.12 mmol) and potassium carbonate (0.3 mmol) were added to acetone (200 ml). The reaction was refluxed for 12 hours. After the reaction was completed, suction filtration was conducted to give organic solution, which was evaporated to dryness under reduced pressure. The residue was applied to column chromatography (eluent: petroleum ether:ethyl acetate=10:1) to give 25.8 g of light yellow oil. Yield: 87%.

MS (ESI) m/z 296.0 ([M+H]$^+$).

(3) The light yellow oil (2 mmol) prepared in step (2), benzylpiperazine (2 mmol) and potassium carbonate (6 mmol) were added to acetonitrile (50 ml). The reaction was refluxed for 10 hours. After the reaction was completed, suction filtration was conducted to give organic solution. Acetonitrile was evaporated to dryness. The residue was applied to column chromatography (eluent: CH$_2$Cl$_2$:methanol=10:1) to give 0.78 g of yellow oil. Yield: 90%.

$^1$H-NMR (600 MHz, CDCl$_3$) δ 1.72-1.88 (m, 4H), 2.49-2.57 (m, 8H), 2.97 (t, 2H, J=12 Hz), 3.59 (s, 3H), 3.61 (s, 2H), 4.09 (t, 2H, J=6 Hz), 7.22-7.35 (m, 4H), 7.63 (d, 2H, J=6 Hz), 7.95 (d, 2H, J=6 Hz). MS (ESI) m/z 407.5 ([M+H]$^+$).

Example 27

6-(4-(3,4-dihydroisoquinolin-2(1H)-yl)butoxy)-3-methylquinazolin-4(3H)-one (27)

The target compound was prepared according to the method of Example 26, using 1,2,3,4-tetrahydroisoquinoline instead of 1-benzylpiperazine as raw material. The structural formula is shown as No. (27) in Table 1.

$^1$H-NMR (600 MHz, CDCl$_3$) δ 1.81-1.95 (m, 4H), 2.60-2.77 (m, 4H), 2.93 (t, 2H, J=12 Hz), 3.59 (s, 3H), 3.61 (s, 2H), 4.12 (t, 2H, J=6 Hz), 7.02-7.14 (m, 4H), 7.63 (d, 2H, J=6 Hz), 7.95 (d, 1H, J=6 Hz). MS (ESI) m/z 364.3 ([M+H]$^+$).

Example 28

3-methyl-6-(4-(4-(3-(trifluoromethyl)phenyl)piperazin-1-yl)butoxy)quinazolin-4(3H)-one (28)

The target compound was prepared according to the method of Example 26, using 1-(3-(trifluoromethyl)phenyl)piperazine instead of 1-benzylpiperazine as raw material. The structural formula is shown as No. (28) in Table 1.

$^1$H-NMR (600 MHz, CDCl$_3$) δ 1.75-1.95 (m, 4H), 2.51 (t, 2H, J=12 Hz), 2.64 (t, 4H, J=12 Hz), 3.27 (t, 4H, J=12 Hz), 3.61 (s, 3H), 4.14 (t, 2H, J=6 Hz), 7.06-7.14 (m, 2H), 7.34-7.37 (m, 2H), 7.65 (d, 2H, J=6 Hz), 7.97 (s, 1H). MS (ESI) m/z 461.3 ([M+H]$^+$).

Example 29

6-(4-(4-(4-fluorophenyl)piperazin-1-yl)butoxy)-3-methylquinazolin-4(3H)-one (29)

The target compound was prepared according to the method of Example 26, using 1-(4-fluorophenyl)piperazine instead of 1-benzylpiperazine as raw material. The structural formula is shown as No. (29) in Table 1.

¹H-NMR (600 MHz, CDCl₃) δ 1.72-1.93 (m, 4H), 2.48 (t, 2H, J=12 Hz), 2.63 (t, 4H, J=12 Hz), 3.12 (t, 4H, J=12 Hz), 3.58 (s, 3H), 4.11 (t, 2H, J=6 Hz), 6.86-6.96 (m, 4H), 7.32-7.37 (m, 2H), 7.65 (d, 1H, J=6 Hz), 7.94 (s, 1H). MS (ESI) m/z 411.2 ([M+H]⁺).

Example 30

3-methyl-6-(4-(4-(pyridin-2-yl)piperazin-1-yl)butoxy)quinazolin-4(3H)-one (30)

The target compound was prepared according to the method of Example 26, using 1-(pyridin-2-yl)piperazine instead of 1-benzylpiperazine as raw material. The structural formula is shown as No. (30) in Table 1.

¹H-NMR (600 MHz, CDCl₃) δ 1.75-1.93 (m, 4H), 2.49 (t, 2H, J=12 Hz), 2.60 (t, 4H, J=12 Hz), 3.57 (t, 4H, J=12 Hz), 3.61 (s, 3H), 4.13 (t, 2H, J=6 Hz), 6.61-6.66 (m, 2H), 7.32-7.36 (m, 1H), 7.46-7.50 (m, 1H), 7.65 (d, 2H, J=6 Hz), 7.96 (s, 1H), 8.19 (d, 1H, J=6 Hz). MS (ESI) m/z 394.3 ([M+H]⁺).

Example 31

2,3-dimethyl-6-(3-(4-(3-(trifluoromethyl)phenyl)piperazin-1-yl)propoxy)quinazolin-4(3H)-one (31)

The target compound was prepared according to the method of Example 26, using 1,3-dibromopropane instead of 1,4-dibromobutane, and 1-(3-(trifluoromethyl)phenyl)piperazine instead of 1-benzylpiperazine as raw material. The structural formula is shown as No. (31) in Table 1.

¹H-NMR (600 MHz, CDCl₃) δ 1.26-1.31 (m, 6H), 2.51 (t, 2H, J=12 Hz), 2.64 (t, 4H, J=12 Hz), 2.82 (s, 3H), 3.27 (t, 4H, J=12 Hz), 3.35-3.50 (m, 3H) 3.65 (s, 3H), 4.17 (t, 2H, J=6 Hz), 7.09-7.21 (m, 3H), 7.34-7.37 (m, 2H), 7.57 (d, 1H, J=6 Hz), 7.63 (d, 1H, J=6 Hz). MS (ESI) m/z 461.3 ([M+H]⁺).

TABLE 1

Numbers and structural formulae of the compounds prepared in Examples 1-31

| No. | Structure |
|---|---|
| 1 | 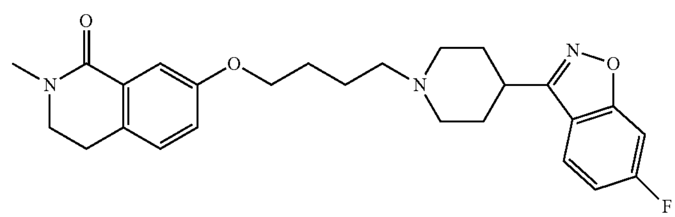 [SMILES: CN1CCc2ccc(OCCCCN3CCC(c4noc5cc(F)ccc45)CC3)cc2C1=O] |
| 2 | 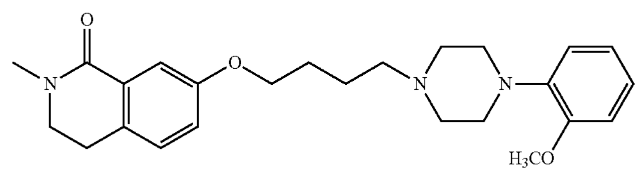 [SMILES: COc1ccccc1N1CCN(CCCCOc2ccc3c(c2)C(=O)N(C)CC3)CC1] |
| 3 | 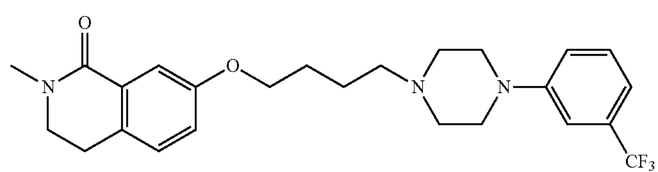 [SMILES: CN1CCc2ccc(OCCCCN3CCN(c4cccc(C(F)(F)F)c4)CC3)cc2C1=O] |
| 4 | 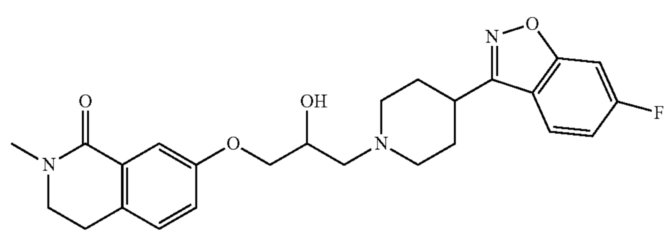 [SMILES: CN1CCc2ccc(OCC(O)CN3CCC(c4noc5cc(F)ccc45)CC3)cc2C1=O] |
| 5 | 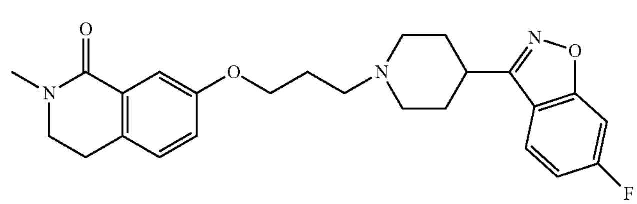 |

TABLE 1-continued

Numbers and structural formulae of the compounds prepared in Examples 1-31

| No. | Structure |
|-----|-----------|
| 6 | 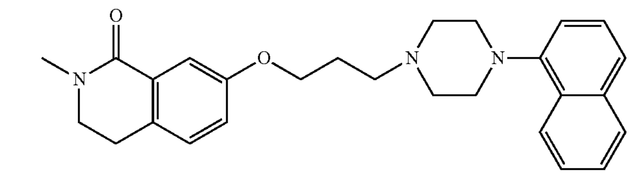 [SMILES: CN1CCc2ccc(OCCCN3CCN(c4cccc5ccccc45)CC3)cc2C1=O] |
| 7 | 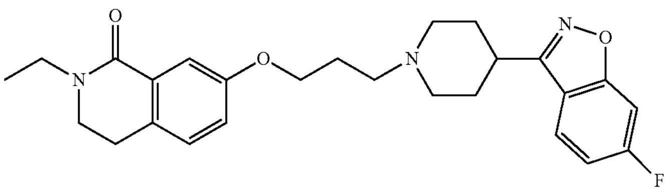 [SMILES: CCN1CCc2ccc(OCCCN3CCC(c4noc5cc(F)ccc45)CC3)cc2C1=O] |
| 8 | 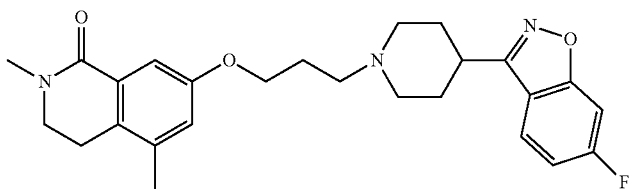 [SMILES: Cc1cc(OCCCN2CCC(c3noc4cc(F)ccc34)CC2)cc2c1CCN(C)C2=O] |
| 9 | 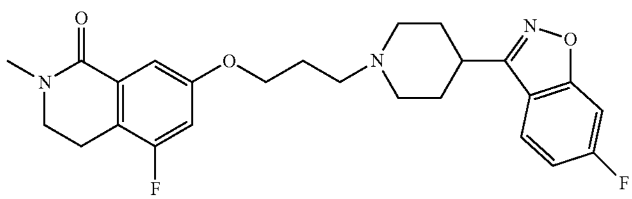 [SMILES: CN1CCc2c(F)cc(OCCCN3CCC(c4noc5cc(F)ccc45)CC3)cc2C1=O] |
| 10 | 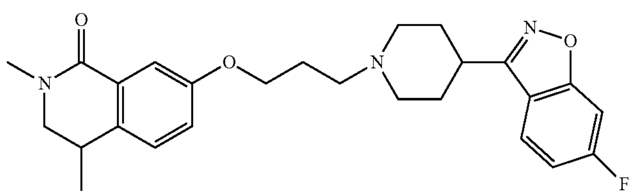 [SMILES: CC1CN(C)C(=O)c2cc(OCCCN3CCC(c4noc5cc(F)ccc45)CC3)ccc21] |
| 11 | 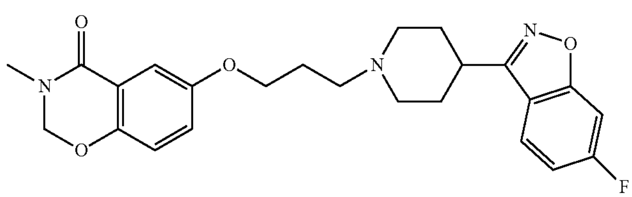 [SMILES: CN1COc2ccc(OCCCN3CCC(c4noc5cc(F)ccc45)CC3)cc2C1=O] |
| 12 | 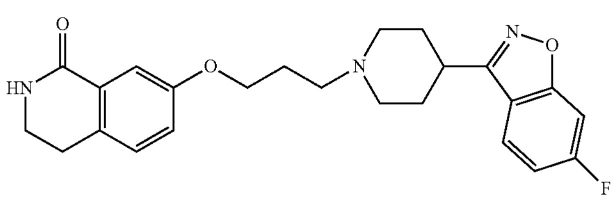 [SMILES: O=C1NCCc2ccc(OCCCN3CCC(c4noc5cc(F)ccc45)CC3)cc21] |

TABLE 1-continued
Numbers and structural formulae of the compounds prepared in Examples 1-31
| No. | Structure |
|---|---|
| 13 | 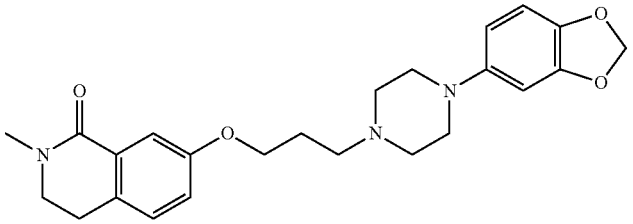 [SMILES: CN1CCc2ccc(OCCCN3CCN(c4ccc5c(c4)OCO5)CC3)cc2C1=O] |
| 14 | 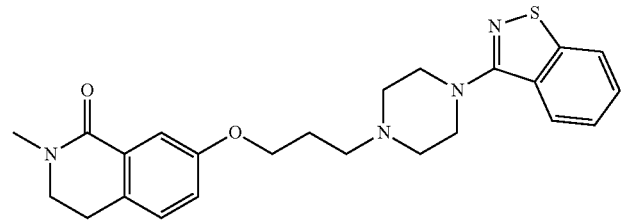 [SMILES: CN1CCc2ccc(OCCCN3CCN(c4nsc5ccccc45)CC3)cc2C1=O] |
| 15 | 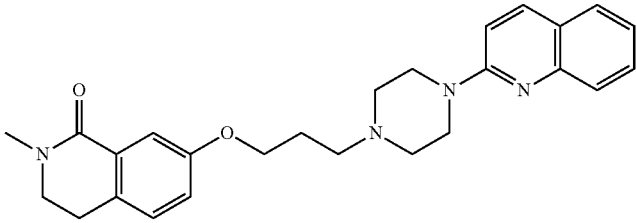 [SMILES: CN1CCc2ccc(OCCCN3CCN(c4ccc5ccccc5n4)CC3)cc2C1=O] |
| 16 | 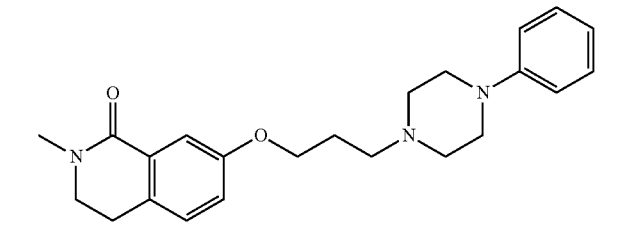 [SMILES: CN1CCc2ccc(OCCCN3CCN(c4ccccc4)CC3)cc2C1=O] |
| 17 | 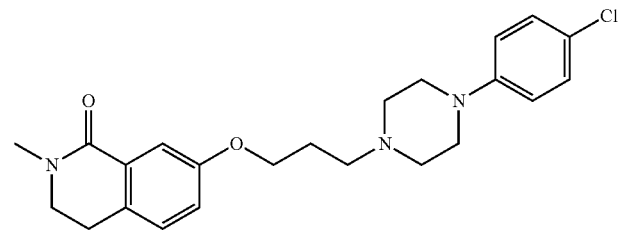 [SMILES: CN1CCc2ccc(OCCCN3CCN(c4ccc(Cl)cc4)CC3)cc2C1=O] |
| 18 | 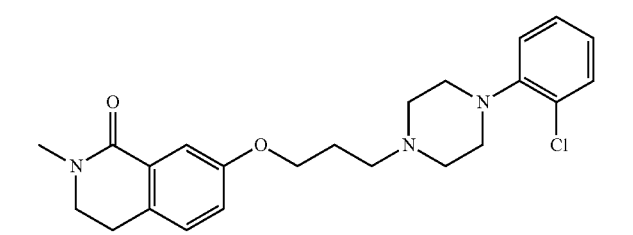 |

TABLE 1-continued

Numbers and structural formulae of the compounds prepared in Examples 1-31

| No. | Structure |
|---|---|
| 19 | 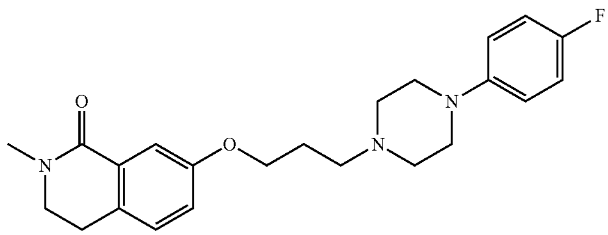 [SMILES: CN1CCc2ccc(OCCCN3CCN(c4ccc(F)cc4)CC3)cc2C1=O] |
| 20 | 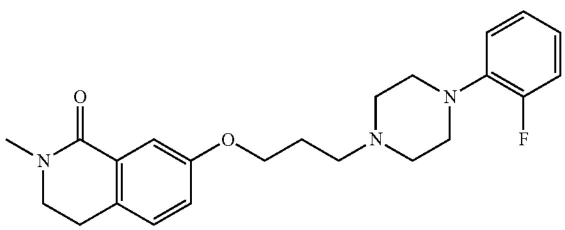 [SMILES: CN1CCc2ccc(OCCCN3CCN(c4ccccc4F)CC3)cc2C1=O] |
| 21 | 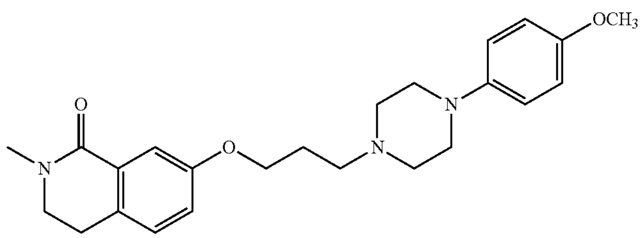 [SMILES: COc1ccc(N2CCN(CCCOc3ccc4c(c3)C(=O)N(C)CC4)CC2)cc1] |
| 22 | 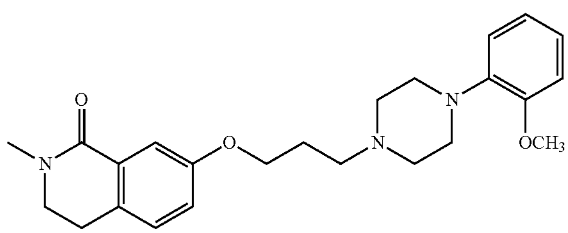 [SMILES: COc1ccccc1N1CCN(CCCOc2ccc3c(c2)C(=O)N(C)CC3)CC1] |
| 23 | 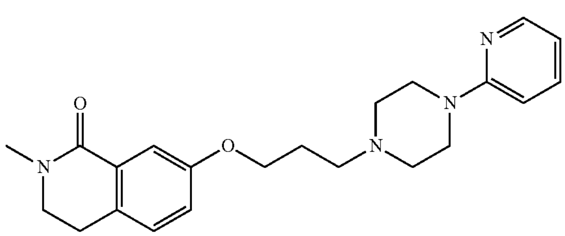 [SMILES: CN1CCc2ccc(OCCCN3CCN(c4ccccn4)CC3)cc2C1=O] |
| 24 | 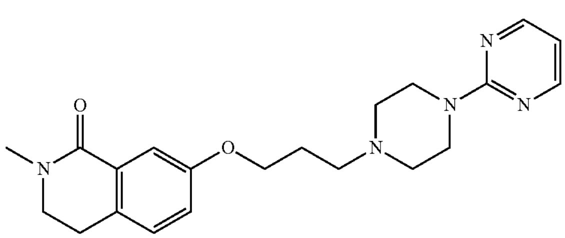 [SMILES: CN1CCc2ccc(OCCCN3CCN(c4ncccn4)CC3)cc2C1=O] |

TABLE 1-continued

Numbers and structural formulae of the compounds prepared in Examples 1-31

| No. | Structure |
|---|---|
| 25 | 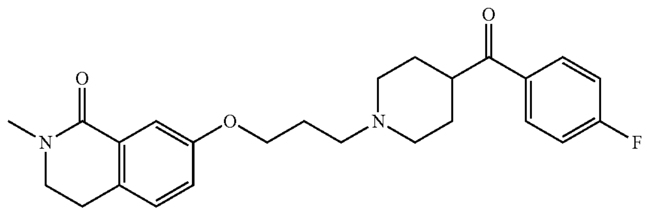 [SMILES: CN1CCc2ccc(OCCCN3CCC(C(=O)c4ccc(F)cc4)CC3)cc2C1=O] |
| 26 | 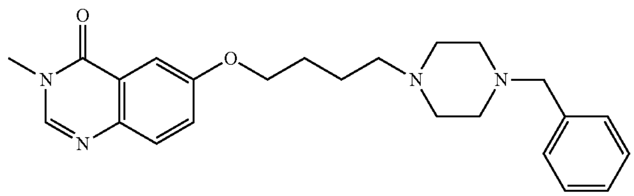 [SMILES: Cn1cnc2ccc(OCCCCN3CCN(Cc4ccccc4)CC3)cc2c1=O] |
| 27 | 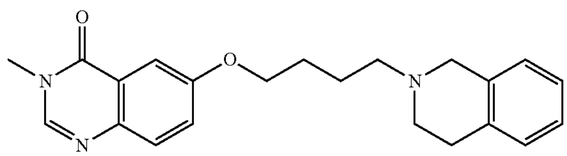 [SMILES: Cn1cnc2ccc(OCCCCN3CCc4ccccc4C3)cc2c1=O] |
| 28 | 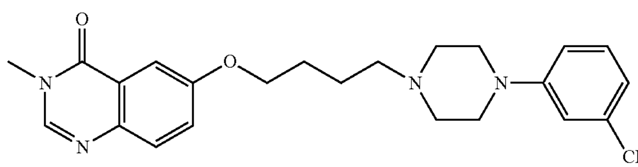 |
| 29 | 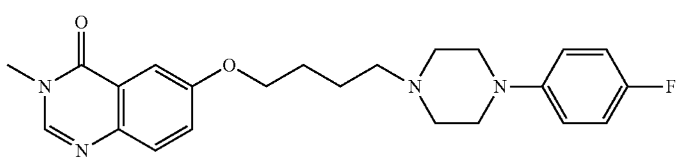 [SMILES: Cn1cnc2ccc(OCCCCN3CCN(c4ccc(F)cc4)CC3)cc2c1=O] |
| 30 | 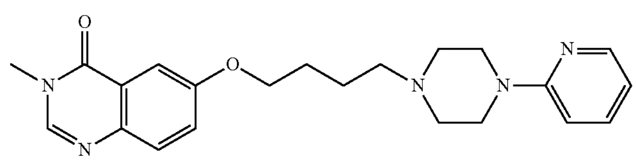 [SMILES: Cn1cnc2ccc(OCCCCN3CCN(c4ccccn4)CC3)cc2c1=O] |
| 31 | 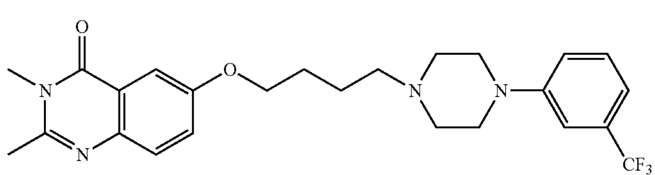 [SMILES: Cc1nc2ccc(OCCCCN3CCN(c4cccc(C(F)(F)F)c4)CC3)cc2c(=O)n1C] |

Pharmacological Examples

Example 32

Preparation of 5-HT$_{1A}$ Membrane

Rats were decapitated. Cortex of brain was rapidly taken on ice, to which 3 ml of buffer (0.05 M Tris-HCl buffer, containing 0.1% ascorbic acid, 10 μM pargyline and 4 mM CaCl$_2$) was added, homogenization was conducted, and then 5 ml of buffer (0.05 M Tris-HCl buffer, containing 0.1% ascorbic acid, 10 μM pargyline and 4 mM CaCl$_2$) was added. Incubation at 37° C. was conducted for 10 min. The weight of the tubes were adjusted using a balance after incubation. Centrifugation was conducted at 12000 rpm, 4° C. for 20 min. The supernatant was discarded, and 3 ml of buffer was added, vortex mixer was used for blending, and then 5 ml of buffer was added. Centrifugation was conducted and repeated 3 times. After the centrifugation, the supernatant was discarded, and the pellets were stored at −80° C. for future use.

Materials for the Receptor Binding Assay

Isotope ligand $^3$H-8-OH-DPAT (67.0 Ci/mmol) was purchased from PerkinElmer Company; 5-HT was purchased from RBI Company; GF/C glass fiber filter paper was purchased from Whatman Company; Tris was imported and divided into aliquots; PPO, POPOP were purchased from Shanghai No. 1 Reagent Factory; liposoluble scintillation cocktail was purchased from Shanghai Reagent Factory; Beckman LS-6500 Multi-function Liquid Scintillation Counter was used.

Procedures (1) The prepared membrane was applied with appropriate amount of buffer, and homogenizer was used for evenly dispersing. 15 tubes were mixed into a 100 ml container, and appropriate amount of buffer was added to give 50 ml of membrane suspension, which was reserved for future use.

(2) 100 μL of membrane preparation and 100 μL of buffer were added into each reaction tube.

(3) 100 μL of buffer was added into the total binding tube (TB), 100 μL of 5-HT (final concentration $10^{-5}$M) was added into the nonspecific binding tube (NB), 100 μL of the test compound (final concentration $10^{-5}$M) was added into the specific binding tube (SB) of each test compound.

(4) 10 μL of radioactive ligand $^3$H-8-OH-DPAT was respectively added into each reaction tube (2 parallel tubes were used for each reaction tube, and each of them was placed on ice when adding sample).

(5) Each reaction tube was incubated at 37° C. for 10 min; after the reaction was completed, the bound ligands were rapidly filtered under reduced pressure, and sufficiently washed with ice-chilled assay buffer. The filter was taken out and put into a 3 ml scintillation vial, and 2 ml of toluene scintillation cocktail was added and blended.

(6) The scintillation vials were put into Liquid Scintillation Counter for counting.

Inhibition rate($I$%)=(Total binding tube cpm−compound cpm)/(Total binding tube cpm−nonspecific binding tube cpm)×100%

Each assay for the compounds was conducted in duplicate for two individual tests. The results are listed in Table 2.

Example 33

Preparation of 5-HT$_{2A}$ Membrane

Rats were decapitated. Cortex of brain was rapidly taken on ice, and 3 ml of buffer (0.05 M Tris-HCl buffer: 6.05 g of Tris was dissolved in 1000 ml of double-distilled water, and concentrated HCl was used to adjust to pH 7.5) was added, homogenization was conducted, and then 5 ml of buffer was added. Incubation was conducted at 37° C. for 10 min, the weight of the tubes were adjusted using a balance after incubation. Centrifugation was conducted at 12000 rpm, 4° C. for 20 min, the supernatant was discarded, and 3 ml of buffer was added. Vortex mixer was used for blending, and then 5 ml of buffer was added. Centrifugation was conducted (repeated 3 times). After the centrifugation, the supernatant was discarded, and the pellets were stored at −80° C. for future use.

Materials for the Receptor Binding Assay

Isotope ligand [$^3$H]-Ketanserin (67.0 Ci/mmol) was purchased from PerkinElmer Company; Methysergide was purchased from RBI Company; GF/C glass fiber filter paper was purchased from Whatman Company; Tris was imported and divided into aliquots; PPO and POPOP were purchased from Shanghai No. 1 Reagent Factory; liposoluble scintillation cocktail was purchased from Shanghai Reagent Factory; Beckman LS-6500 Multi-function Liquid Scintillation Counter was used.

Procedures (1) The prepared membrane was applied with buffer, and homogenizer was used for evenly dispersing. 15 tubes were mixed into a 100 ml container, and appropriate amount of buffer was added to give 50 ml of membrane suspension, which was reserved for future use.

(2) 100 μL of membrane preparation and 100 μL of buffer were added into each reaction tube.

(3) 100 μL of buffer was added into the total binding tube (TB), 100 μL of Methysergide (final concentration $10^{-5}$M) was added into the nonspecific binding tube (NB), 100 μL of the test compound (final concentration $10^{-5}$M) was added into the specific binding tube (SB) of each test compound.

(4) 10 μL of radioactive ligand $^3$H-Ketanserin was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and sufficiently washed with ice-chilled assay buffer. The filter was taken out and put into a 3 ml scintillation vial, and 2 ml of toluene scintillation cocktail was added and blended.

(6) The scintillation vial were put into Liquid Scintillation Counter for counting.

Inhibition rate($I$%)=(Total binding tube cpm−compound cpm)/(Total binding tube cpm−nonspecific binding tube cpm)×100%

Each assay for the compounds was conducted in duplicate for two individual tests. The results are listed in Table 2.

Example 34

Preparation of D$_2$ Membrane

Rats were decapitated. Striatum of brain was rapidly taken on ice, 3 ml of buffer (0.05 M Tris-HCl buffer, containing NaCl 120 mM, KCl 5 mM, MgCl$_2$ 1 mM, CaCl$_2$ 1 mM) was added, homogenization was conducted, and then 5 ml of buffer was then added. The weight of the homogenized tubes were adjusted using a balance, and centrifugation was conducted. The supernatant was discarded, and 3 ml of buffer was added. Vortex mixer was used for blending, and then 5 ml of buffer was added. Centrifugation was conducted and repeated 3 times. The supernatant was discarded after centrifugation was completed, and the pellets were stored at −80° C. for future use.

Materials for the Receptor Binding Assay

Isotope ligand $^3$H-Spiperone (67.0 Ci/mmol) was purchased from PerkinElmer Company; Butaclamol was purchased from RBI Company; GF/C glass fiber filter paper was purchased from Whatman Company; Tris was imported and divided into aliquots; PPO and POPOP were purchased from Shanghai No. 1 Reagent Factory; liposoluble scintillation cocktail was purchased from Shanghai Reagent Factory. Beckman LS-6500 Multi-function Liquid Scintillation Counter was used.

Procedures (1) The prepared membrane was applied with appropriate amount of buffer, and homogenizer was used for evenly dispersing. 15 tubes were mixed into a 100 ml container, and appropriate amount of buffer was added to give 50 ml of membrane suspension, which was reserved for future use.

(2) 100 μL of membrane preparation and 100 μL of buffer were added into each reaction tube.

(3) 100 μL of buffer was added into the total binding tube (TB), 100 μL of Butaclamol (final concentration $10^{-5}$M) was added into the nonspecific binding tube (NB), 100 μL of the test compound (final concentration $10^{-5}$M) was added into the specific binding tube (SB) of each test compound.

(4) 10 μL of radioactive ligand $^3$H-Spiperone was respectively added into each reaction tube (2 parallel tubes were used for each reaction tube, and each of them was placed on ice when adding sample).

(5) Each of the reaction tubes was incubated at 37° C. for 20 min. After the reaction was completed, the bound ligands were rapidly filtered under reduced pressure, and sufficiently washed with ice-chilled assay buffer. The filter was taken out and put into a 3 ml scintillation vial, and 2 ml of toluene scintillation cocktail was added and blended.

(6) The scintillation vials were put into Liquid Scintillation Counter for counting.

Inhibition rate($I\%$)=(Total binding tube cpm–compound cpm)/(Total binding tube cpm–nonspecific binding tube cpm)×100%

Each assay for the compounds was conducted in duplicate for two individual tests. The results are listed in Table 2.

Example 35 5-HT$_7$ Receptor Binding Assay

Preparation of 5-HT$_7$ Membrane

Adult SD rats were decapitated. Hypothalamus was rapidly taken on ice, and 3 ml of buffer (0.05 M Tris-HCl buffer: 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation was conducted at 37° C. for 10 min, the weight of the tubes were adjusted using a balance after incubation. Centrifugation was conducted at 4° C., the supernatant was discarded, and 3 ml of buffer was added. Vortex mixer was used for blending, and then 5 ml of buffer was added. Centrifugation was conducted (repeated 3 times). After the centrifugation, the supernatant was discarded, and the pellets were stored at −80° C. for future use.

Materials for the Receptor Binding Assay

Isotope ligand [$^3$H]-5-CT (85.4 Ci/mmol) was purchased from PerkinElmer Company; (±)-pindolol was purchased from RBI Company; GF/C glass fiber filter paper was purchased from Whatman Company; Tris was imported and divided into aliquots; PPO and POPOP were purchased from Shanghai No. 1 Reagent Factory; liposoluble scintillation cocktail was purchased from Shanghai Reagent Factory. Beckman LS-6500 Multi-function Liquid Scintillation Counter was used.

Procedures (1) The prepared membrane was applied with buffer, and homogenizer was used for evenly dispersing. 15 tubes were mixed into a 100 ml container, and appropriate amount of buffer was added to give 50 ml of membrane suspension, which was reserved for future use.

(2) 100 μL of membrane preparation and 100 μL of buffer were added into each reaction tube.

(3) 100 μL of buffer was added into the total binding tube (TB), 100 μL of (±)-pindolol (final concentration $10^{-5}$M) was added into the nonspecific binding tube (NB), 100 μL of the test compound (final concentration $10^{-5}$M) was added into the specific binding tube (SB) of each test compound.

(4) 10 μL of radioactive ligand $^3$H-5-CT was respectively added into each reaction tube (2 parallel tubes were used for each reaction tube, and each of them was placed on ice when adding sample).

(5) Each of the reaction tubes was incubated at 25° C. for 120 min. After the reaction was completed, the bound ligands were rapidly filtered under reduced pressure, and sufficiently washed with ice-chilled assay buffer. The filter was taken out and put into a 3 ml scintillation vial, and 2 ml of toluene scintillation cocktail was added and blended.

(6) The scintillation vials were put into Liquid Scintillation Counter for counting.

Inhibition rate($I\%$)=(Total binding tube cpm–compound cpm)/(Total binding tube cpm–nonspecific binding tube cpm)×100%

Each assay for the compounds was conducted in duplicate for two individual tests. The results are listed in Table 2.

Example 36

Preparation of Histamine H$_1$ Receptor Membrane

Guinea pigs were decapitated. Cerebellum of the guinea pig was rapidly taken on ice and 3 mL of buffer (potassium dihydrogen phosphate 1.36 g, 0.1 mol/L sodium hydroxide 79 ml, metered to 200 ml with double-distilled water) was added. Vortex mixer was used for blending. Centrifugation was conducted at 48000 g, 4° C. for 10 min. The supernatant was discarded to give pellets, and buffer was added again for washing. Centrifugation was conducted and repeated 3 times. After the centrifugations, the supernatant was discarded, and the pellets were stored at −80° C. for future use.

Materials for the Receptor Binding Assay

Isotope ligand $^3$H-pyrilamine (67.0 Ci/mmol) was purchased from PerkinElmer Company; promethazine was purchased from RBI Company; GF/C glass fiber filter paper was purchased from Whatman Company; Tris was imported and divided into aliquots; PPO, POPOP were purchased from Shanghai No. 1 Reagent Factory; liposoluble scintillation cocktail was purchased from Shanghai Reagent Factory; Beckman LS-6500 Multi-function Liquid Scintillation Counter was used.

Procedure (1) The prepared membrane was applied with appropriate amount of buffer, and homogenizer was used for evenly dispersing. 15 tubes were mixed into a 100 ml container, and appropriate amount of buffer (potassium dihydrogen phosphate 1.36 g, 0.1 mol/L sodium hydroxide 79 ml, metered to 200 ml with double-distilled water) was added to give 50 ml of membrane suspension, which was reserved for future use.

(2) 100 μL of membrane preparation was added into each reaction tube.

(3) 100 μL of buffer was added into the total binding tube (TB), 100 μL of promethazine (final concentration $10^{-5}$M) was added into the nonspecific binding tube (NB), 100 μL of the test compound (final concentration $10^{-5}$M) was added into the specific binding tube (SB) of each test compound.

(4) 10 μL of radioactive ligand $^3$H-pyrilamine was respectively added into each reaction tube (2 parallel tubes were used for each reaction tube, and each of them was placed on ice when adding sample).

(5) Each of the reaction tubes was incubated at 30° C. for 60 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate($I\%$)=(Total binding tube cpm−compound cpm)/(Total binding tube cpm−nonspecific binding tube cpm)×100%

Each assay for the compounds was conducted in duplicate for two individual tests. The results are listed in Table 2.

TABLE 2

The Ki (nM) of the compounds to the receptors

| Compound No. | $D_2$ | $HT_{1A}$ | $5\text{-}HT_{2A}$ | $5\text{-}HT_7$ | $H_1$ |
|---|---|---|---|---|---|
| 1 | 12.5 | 15.8 | 18.9 | 12.5 | — |
| 2 | 120 | 11.3 | 36.8 | — | — |
| 3 | 17.2 | 11.8 | 9.9 | 23.6 | — |
| 4 | 15.1 | 3.9 | 15.9 | 10.2 | >2000 |
| 5 | 1.0 | 2.4 | 0.1 | 5.9 | >2000 |
| 6 | 134.2 | 46.6 | 57.0 | — | — |
| 7 | 13.1 | 1.9 | 0.9 | 12.7 | >2000 |
| 8 | 8.7 | 2.8 | 2.4 | 6.7 | >2000 |
| 9 | 3.1 | 3.9 | 3.7 | 7.9 | >2000 |
| 10 | 5.8 | 4.6 | 12.9 | 8.4 | >2000 |
| 11 | 13.9 | 24.6 | 3.6 | 11.2 | >2000 |
| 12 | 10.4 | 19.3 | 5.5 | 8.9 | >2000 |
| 13 | 234.7 | 12.8 | 3.6 | — | — |
| 14 | 6.9 | 8.8 | 7.2 | 16.8 | 1357.9 |
| 15 | 1987.3 | 156.8 | 467.9 | — | — |
| 16 | >2000 | 568.9 | 372.1 | — | — |
| 17 | >2000 | >2000 | >2000 | — | — |
| 18 | >2000 | >2000 | >2000 | — | — |
| 19 | 1654.1 | 746.2 | 688.3 | — | — |
| 20 | 54.8 | 24.5 | 32.1 | 29.9 | >2000 |
| 21 | >2000 | >2000 | >2000 | — | — |
| 22 | 9.6 | 6.5 | 3.2 | 28.1 | >2000 |
| 23 | >2000 | >2000 | 368.9 | — | — |
| 24 | 11.9 | 8.8 | 7.5 | 9.9 | >2000 |
| 25 | 32.8 | 17.6 | 21.7 | 10.8 | >2000 |
| 26 | >2000 | 56.9 | >2000 | — | — |
| 27 | 499.8 | 57.9 | 66.2 | — | — |
| 28 | 24.8 | 12.2 | 5.8 | 7.4 | >2000 |
| 29 | >2000 | 258.7 | 347.2 | — | — |
| 30 | >2000 | >2000 | >2000 | — | — |
| 31 | 21.8 | 19.0 | 9.8 | 8.3 | >2000 |
| A | 21.2 | 14.3 | 29.2 | 254.2 | 89.6 |
| B | 15.1 | | | 579.3 | 139.2 |
| C | 35.2 | | | 499.7 | 137.8 |
| D | 25.5 | | | 606.4 | 154.3 |
| E | 5.6 | 23.2 | 12.7 | 35.6 | 178.3 |
| risperidone | 11.63 | 170.85 | 3.55 | 12.8 | 168.8 |

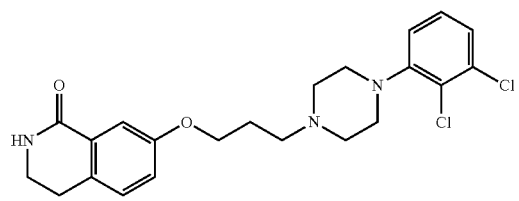

Compound A

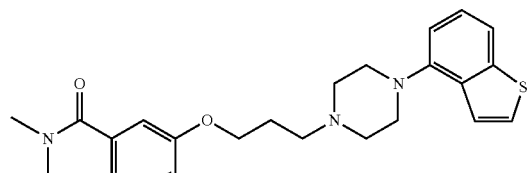

Compound B

Compound C

Compound D

Compound E

The results indicate that the compound of the invention (in particular compound 5) has strong affinities for three receptors ($D_2$, $5\text{-}HT_{1A}$ and $5\text{-}HT_{2A}$), low affinity for $H_1$, and high affinity for $5HT_7$. The risk of the side effect of body-weight gain is low, as compared with risperidone. $5HT_7$ receptor can modulate emotion, learning, as well as memory and action with such receptor may contribute to function of improvement of cognitive disorders.

Example 37: MK-801 Induced High Activity—In Vivo Anti-Schizophrenia Activity of the Compounds Animals and Reagents Healthy mice of Kunming breed, with half male and half female, body weight of (20±2) g, were provided by Qinglongshan Animal Cultivation Center, Nanjing.

Ascorbic acid was provided by Sinopharm Chemical Reagent Co. Ltd.

MK-801 was produced by Sigma Company, USA; the formulation method: 0.1% vitamin C was used to formulate a 1 mg/ml solution.

Test positive drugs: haloperidol, clozapine, risperidone, olanzapine, aripiprazole, ziprasidone, quetiapine.

Tween 80: with the concentration of 10%.

Procedures

Mice with qualified body weight were selected, and randomly divided into blank group, model group, positive control group (risperidone group) and drug group. 10% Tween was administered intragastrically to the blank group and the model group at 0.1 ml/10 g; risperidone was administered intragastrically to the positive control group at 0.1 mg/kg; and corresponding amounts of drugs were administered intragastrically to the drug groups, respectively. 1 h after the administration, 0.1% concentration of ascorbic acid was intraperitoneally injected to the blank group at 0.1 ml/10 g; and the model group, the positive control group (30 min) and the drug group were intraperitoneally injected the MK-801 solution at 0.1 mg/kg. Subsequently, the spontaneous activities of the mice of each group in 90 min were measured. The results are listed in Table 3.

Example 38: Apomorphine Induced Clambering Assay of Mice

Animals

Healthy KM mice, male, with body weight of 18-22 g, were provided by Qinglongshan Animal Cultivation Center, Nanjing.

Main Reagents

Test positive drugs: haloperidol, clozapine, risperidone, olanzapine, aripiprazole, ziprasidone, quetiapine.

Apomorphine provided by Sigma Company was dissolved in 0.9% NaCl (containing 0.1% vitamin C) before use, and was freshly formulated before use.

Vitamin C, F20061113, was provided by Sinopharm Chemical Reagent Co. Ltd.

Sodium chloride injection, H32026305, was provided by Xuzhou No. 5 Pharmaceutical Factory Co. Ltd.

Instruments: self-made clambering cage, chronograph.

Procedures: apomorphine induced clambering assay of mice

KM mice (male, with body weight of 18-22 g) were randomly divided into negative control group, model group, positive drug groups of each dosage (risperidone, aripiprazole, ziprasidone, quetiapine, olanzapine, haloperidol, clozapine), and compound groups of each dosage (the specific dosages are listed in the following Table), with 10 mice of each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups of each dosage, with the volume for intragastric administration as 0.1 ml/10 g. 1 hour after the intragastric administration, apomorphine was subcutaneously injected (1 mg/kg), with the volume as 0.1 ml/10 g. After the injection of apomorphine, the animals were immediately put into the clambering cages. After 5 min of adaptation, the behavior of the mice at 10-11, 20-21, and 30-31 min after the injection of apomorphine were observed and scored. Scoring criteria: the behavior of 4 paws on the floor was scored as 0; the behavior of 2 forepaws on the cage was scored as 1; and the behavior of 4 paws on the cage was scored as 2. The results are listed in Table 3.

Example 39 Conditioned Avoidance Response (CAR) Model Assay of Rat

Animals

About 1700 of SD rats, male.

Firstly, training the rats with shuttle box:

① The rats were allowed for adaption for five minutes;
② Conditioned stimulus (CS, light and noise) were started and lasted for 20 s, and at the tenth second, unconditioned stimulus (US, 1.5 mA electric shock) was performed and lasted for 10 s;
③ Training was conducted 30 times per day for 9 days. The interval between two trainings was set randomly ranged from 20 to 30 s;
④ Observation indicators:

The animal ran to another compartment during the conditioning stimulus was recorded as "avoidance";

Animals ran to another compartment during the electric shock was recorded as "escape";

Animals did not run to another compartment during the electric shock was recorded as an "escape failure";

⑤ Criteria for qualified training: The avoidance rate is greater than 80% for 3 consecutive days (the 7th, 8th, and 9th days).

Grouping of the qualified rats: the qualified rats were divided into negative control group, positive drug groups of each dosage, and compound groups of each dosage according to the principle of randomization, 8 in each group.

Administration Method: Corresponding solvent was administered intragastrically to the negative control group; corresponding dosages of positive drugs were administered intragastrically to the positive drug groups of each dosage; and corresponding dosages of compounds were administered intragastrically to the compound groups of each dosage.

CAR Assay: A CAR assay was performed 1 hour after intragastric administration. The method was the same as the CAR training. The observation indicators were the number of avoidances, the number of escapes, and the number of escape failures.

Statistical Data Processing: Assay data are presented as mean±standard deviation (Mean±SD), the comparison was performed by a combination of one-way ANOVA with post-hoc LSD. The $ED_{50}$ was calculated using the probit method. The results are listed in Table 4.

Example 40: Catalepsy Assay

Animals

Healthy mice of Kunming breed, with half male and half female, body weight of (22±2) g, were provided by Qinglongshan Animal Cultivation Center, Nanjing.

Main reagents: the test drugs, haloperidol, clozapine, risperidone, olanzapine, aripiprazole, ziprasidone.

Instruments: self-made bar-grabbing apparatus, stainless steel bar in mice box, which was 0.3 cm in diameter and 5 cm above the bench.

Procedures

KM mice (half male and half female, with body weight of 20-24 g) were randomly divided into negative control group, model group, positive drug groups of each dosage (risperidone, aripiprazole, ziprasidone, quetiapine, olanzapine, haloperidol, clozapine), compound groups of each dosage, with 10 mice in each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), corresponding dosages of compounds were administered intragastrically to the compound groups for each dosage, with the volume for intragastric administration as 0.1 ml/10 g. At 30 min, 60 min, 90 min after the intragastric administration, the two forepaws of the mice were gently placed on the bars (which were 20 cm in length, 0.3 cm in diameter, and 5.5 cm above the bench), and the hindpaws of the animals were placed on the bottom of the box. The durations of the mice to maintain the posture with the two forepaws on the bars were recorded, and 30 s of spasticity without moving was considered as the positive response. In the case the forepaws of the mice were not put down persistently, the observation was terminated at 60 s. The numbers of animals with positive response in each of the compound dosage groups were counted. The results are listed in Table 3.

Example 41: Acute Toxicity Study

Limit test of sequential assay: KM rats or mice (half male and half female) were randomly divided into several groups (with 2-5 mice in each group), which were respectively the 2000 mg/kg groups for each compound, and the solvent group. 0.2 ml/10 g were administered intragastrically. The deaths of the animals in 3 days were observed. In the case 3 or more animals survived in 3 days without notable abnormity in their life states, the observation was continued until the assay was completed in 7 days. In the case 3 or more animals died in 3 days, the method of median lethal dose was used to determine the $LD_{50}$.

Pre-assay for the method of the median lethal dose: KM mice (half male and half female) were randomly divided into several groups (with 4 mice in each group), which were respectively the 500 mg/kg, 200 mg/kg, 50 mg/kg groups for each compound, and the solvent group. 0.2 ml/10 g were administered intragastrically, and the deaths of the animals in 1-3 days were observed.

Results: The compound of the invention has relatively low acute toxicity. For example, the $LD_{50}$ of intragastric administration of the compound 5 in mice is 257.5 mg/kg, and the $LD_{50}$ of intragastric administration of the same in rats is 167.5 mg/kg. The therapeutic index is significantly greater than the positive drug risperidone, indicating a relatively low acute toxicity. The results are listed in Table 3 and Table 4.

activity, but also effectively improve the apomorphine induced clambering symptoms. Meanwhile, they performed markedly better than risperidone in the rat CAR model, and they do not cause EPS in effective dosage, indicating notable anti-schizophrenia effects, as well as superior effects over the prior drugs.

Formulation Example

Example 42 Preparation of the Tablet Dosage

| | |
|---|---|
| Active Ingredient | 100 mg |
| (any one of the compounds 1~31 of the invention) | |
| microcrystalline cellulose | 50 mg |
| lactose | 100 mg |
| Povidone K30 | 9 mg |
| carboxymethyl starch sodium | 12 mg |
| silica | 2.5 mg |
| magnesium stearate | 1.5 mg |

The raw excipients were sieved with 80 mesh for use. The prescription doses of active ingredient, microcrystalline cellulose, lactose, Povidone K30 were weighed and introduced into a high speed mixing granulator, whereby they were mixed uniformly at low speed. An appropriate amount of purified water was added, the stirring was performed at low speed, and high speed shear granulation was carried out. The wet granules were dried at 60° C. for 3 hours, and sieved with 24 mesh. The prescription doses of carboxymethyl starch sodium, silica and magnesium stearate were added for mixing totally. The compression was performed in a rotary tablet press.

TABLE 3

Results of the in vivo animal model assay of the compounds (mice)

| Compound No. | $LD_{50}$ (po, mg/kg) | MK-801 induced high activity ($ED_{50}$, po, mg/kg) | Apomorphine induced clambering ($ED_{50}$, po, mg/kg) | Catalepsy ($ED_{50}$, po, mg/kg) | Catalepsy/ MK-801 induced high activity | Catalepsy/ Apomorphine induced clambering |
|---|---|---|---|---|---|---|
| 5 | 257 | 0.04 | 0.05 | 35 | 875 | 700 |
| 14 | 202 | 0.07 | 0.06 | 32 | 457 | 533 |
| 22 | 311 | 0.12 | 0.19 | 52 | 433 | 273 |
| 24 | 190 | 0.18 | 0.22 | 47 | 261 | 214 |
| haloperidol | 20 | 0.10 | 0.08 | 0.44 | 4.40 | 4.89 |
| clozapine | 150 | 2.28 | 17.92 | >50 | >21.93 | >5.58 |
| risperidone | 82.1 | 0.01 | 0.046 | 0.97 | 92.00 | 61.33 |

TABLE 4

Results of the rats CAR assay

| Compound No. | Rat CAR $ED_{50}$ (mg/kg) | Rat $LD_{50}$ (mg/kg) | Therapeutic index |
|---|---|---|---|
| 5 | 0.32 | 167.5 | 523 |
| 14 | 0.65 | 155 | 238 |
| 22 | 0.49 | 198 | 404 |
| 24 | 1.02 | 146 | 143 |
| risperidone | 0.66 | 113 | 171 |

The above results of animal assays indicate that, when compared with the positive drug (risperidone), the compound of the invention (in particular compounds 5, 14, 22) can not only significantly improve the MK-801 induced high

The invention claimed is:
1. A compound of Formula I or a pharmaceutically acceptable salt or prodrug thereof:

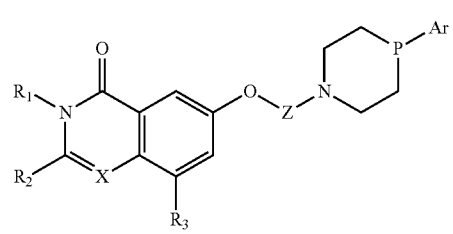

I wherein,

X is C, O, N or NH;

Z is -(CH$_2$)$_n$—, which is unsubstituted or substituted by one or more substituents selected from the group consisting of alkyl, cyano, hydroxy and halogen, n is an integer of 2~7;

R$_1$ and R$_2$ are each independently hydrogen, linear or branched alkyl containing 1~5 carbon atoms, wherein the alkyl is optionally substituted by one or more substituents selected from the group consisting of alkyl, cyano, hydroxy and halogen;

R$_3$ is hydrogen, halogen or linear or branched alkyl containing 1~5 carbon atoms, wherein the alkyl is optionally substituted by one or more substituents selected from the group consisting of alkyl, cyano, hydroxy and halogen;

P is CH or N;

Ar is a group selected from the group consisting of formula II-VII:

II

III

IV

V

VI

VII

L and M are independently CH or N;

Q is O or S;

R$_6$, R$_7$ and R$_8$ are each independently hydrogen, halogen, linear or branched alkyl containing 1~5 carbon atoms, or alkoxyl containing 1~5 carbon atoms, wherein the alkyl is optionally substituted by one or more substituents selected from the group consisting of alkyl, cyano, hydroxy and halogen, and wherein the alkoxyl is optionally substituted by one or more substituents selected from the group consisting of alkyl, cyano, hydroxy and halogen;

R$_4$, R$_5$ are each independently hydrogen, halogenated C$_{1-5}$ alkyl, methoxyl, ethoxyl or propoxy.

2. The compound according to claim 1 or the pharmaceutically acceptable salt or prodrug thereof, wherein, R$_1$ and R$_2$ are each independently hydrogen, methyl, ethyl, propyl, n-butyl, iso-butyl, trifluoromethyl, trifluoroethyl or trifluoropropyl.

3. The compound according to claim 1 or the pharmaceutically acceptable salt or prodrug thereof, wherein, R$_3$ is hydrogen, fluorine, chlorine, bromine, iodine, methyl, ethyl, propyl, n-butyl or iso-butyl.

4. The compound according to claim 1 or the pharmaceutically acceptable salt or prodrug thereof, wherein, R$_8$ is hydrogen, halogenated C$_{1-5}$ alkyl, methoxyl, ethoxyl, propoxy, chlorine, fluorine or bromine.

5. The compound according to claim 4 or the pharmaceutically acceptable salt or prodrug thereof, wherein, the halogenated C$_{1-5}$ alkyl is trifluoromethyl, trifluoroethyl, trifluoropropyl or trifluorobutyl.

6. The compound according to claim 1 or the pharmaceutically acceptable salt or prodrug thereof, wherein, the halogen is independently fluorine, chlorine, bromine or iodine.

7. The compound according to claim 1 or the pharmaceutically acceptable salt or prodrug thereof, wherein, X is C, O, N or NH;

Z is -(CH$_2$)$_n$—, which is unsubstituted or substituted by one or more hydroxy, n is an integer of 2~5;

R$_1$ is hydrogen, methyl or ethyl;

R$_2$ is hydrogen, methyl or ethyl;

R$_3$ is hydrogen, methyl or fluorine.

8. A compound or the pharmaceutically acceptable salt or prodrug thereof, wherein, the compound is selected from

1

2

3

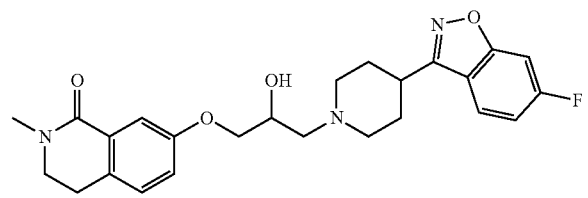
4
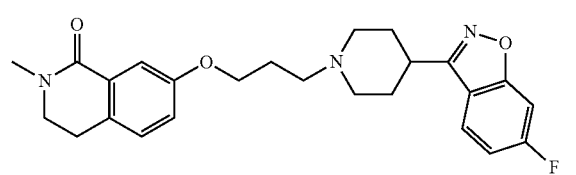
5
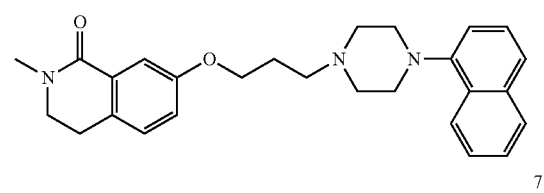
6
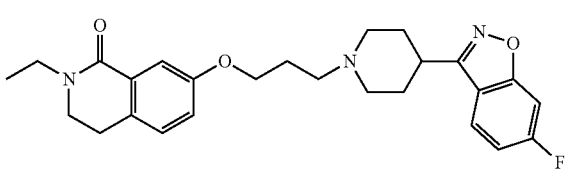
7
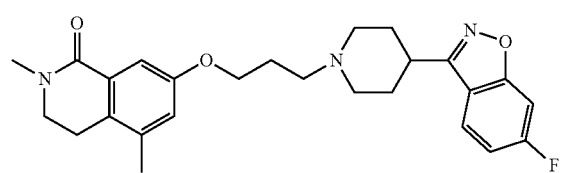
8
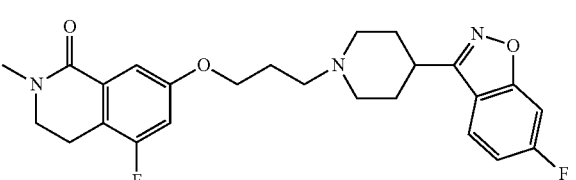
9
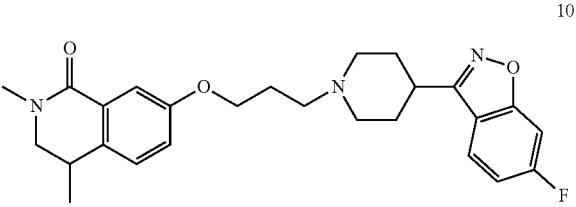
10
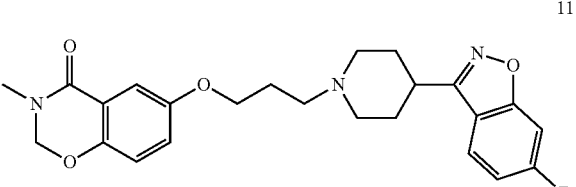
11
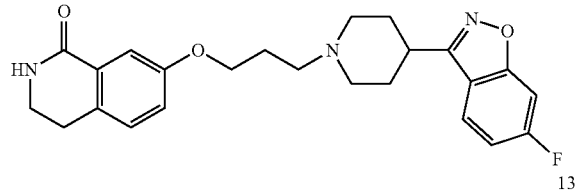
12
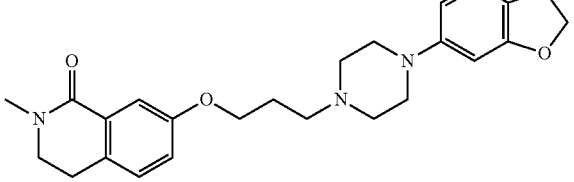
13
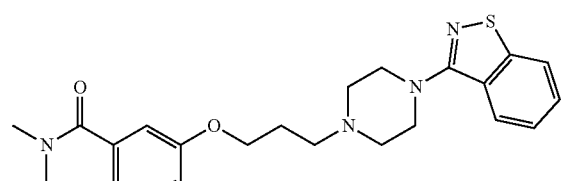
14
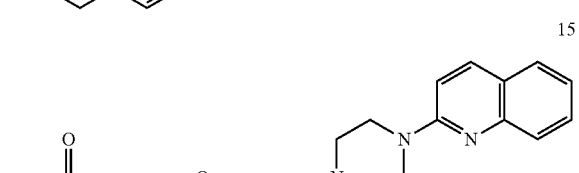
15
16
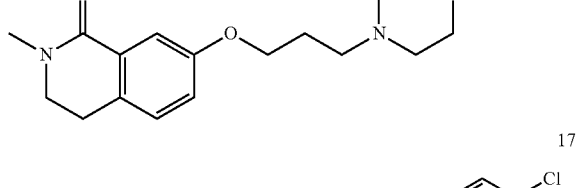
17
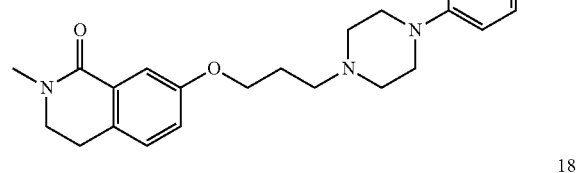
18
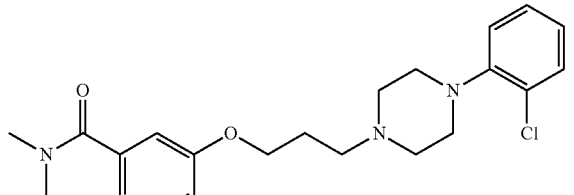

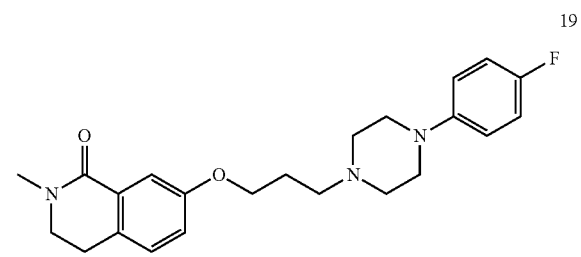

19

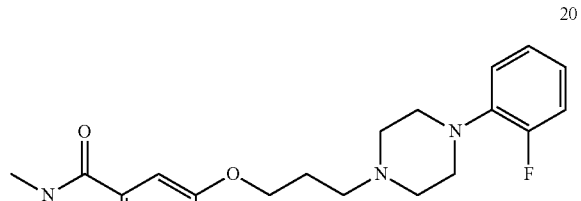

20

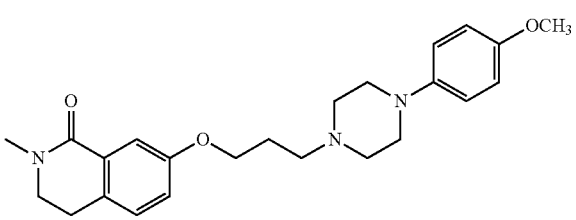

21

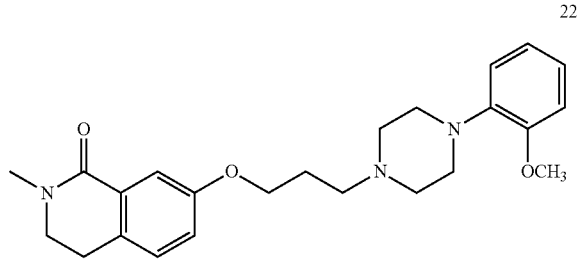

22

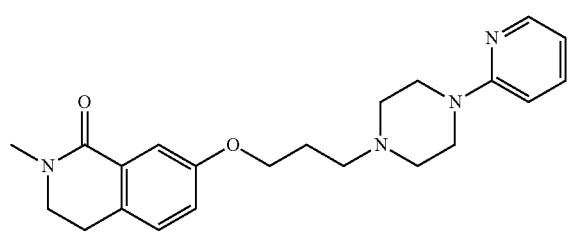

23

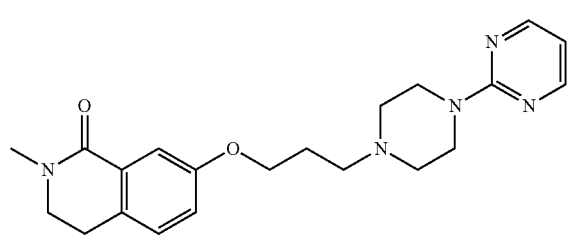

24

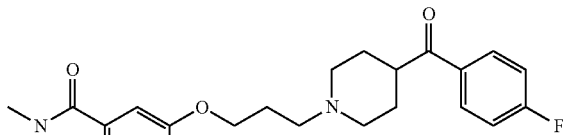

25

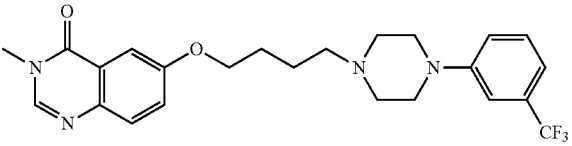

28

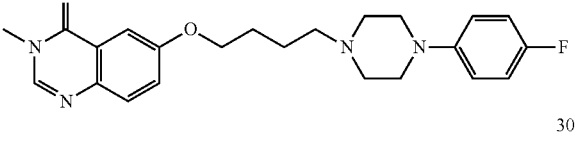

29

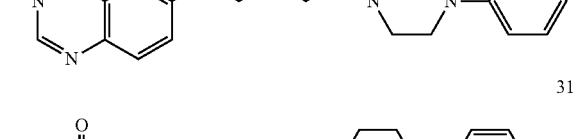

30

31

9. A pharmaceutical composition, comprising the compound according to claim 1 or the pharmaceutically acceptable salt or prodrug thereof, and a pharmaceutically acceptable excipient, carrier, adjuvant, solvent or the combination thereof.

10. A method for the treatment of schizophrenia comprising administering to a subject having said disease the compound according to claim 1 or the pharmaceutically acceptable salt or prodrug thereof in an effective amount.

11. A method for the treatment of schizophrenia comprising administering to a subject having said disease the pharmaceutical composition according to claim 9 in an effective amount.

12. A pharmaceutical composition comprising the compound according to claim 8 or the pharmaceutically acceptable salt or prodrug thereof, and a pharmaceutically acceptable excipient, carrier, adjuvant, solvent or the combination thereof.

13. A method for the treatment of schizophrenia comprising administering to a subject having said disease an effective amount the compound according to claim 8 or the pharmaceutically acceptable salt or prodrug thereof.

14. A method for the treatment of schizophrenia comprising administering to a subject having said disease an effective amount of the pharmaceutical composition according to claim 12.

* * * * *